(12) United States Patent
Chung et al.

(10) Patent No.: US 10,416,116 B2
(45) Date of Patent: Sep. 17, 2019

(54) ACTIVE TRANSPORT OF CHARGED MOLECULES INTO, WITHIN, AND/OR FROM CHARGED MATRICES

(71) Applicant: Massachusetts Institute of Technology, Cambridge, MA (US)

(72) Inventors: Kwanghun Chung, Cambridge, MA (US); Sung-Yon Kim, Cambridge, MA (US); Kimberly Ohn, Boston, MA (US); Evan Murray, Cambridge, MA (US); Jae Hun Cho, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 498 days.

(21) Appl. No.: 14/678,660

(22) Filed: Apr. 3, 2015

(65) Prior Publication Data
US 2015/0285765 A1    Oct. 8, 2015

Related U.S. Application Data

(60) Provisional application No. 61/975,575, filed on Apr. 4, 2014.

(51) Int. Cl.
*G01N 27/447*    (2006.01)

(52) U.S. Cl.
CPC .  *G01N 27/44756* (2013.01); *G01N 27/44704* (2013.01); *G01N 27/44708* (2013.01); *G01N 27/44713* (2013.01)

(58) Field of Classification Search
CPC ............ C12Q 2565/125; G01N 33/561; B01D 57/02; C07K 1/26; C07K 1/28;
(Continued)

(56) References Cited

U.S. PATENT DOCUMENTS

| 4,205,059 A | 5/1980 | von Hagens |
| 4,244,992 A | 1/1981 | von Hagens |

(Continued)

FOREIGN PATENT DOCUMENTS

| AU | 2004241591 A1 | 12/2014 |
| CN | 103353476 A | 10/2013 |

(Continued)

OTHER PUBLICATIONS

Invitation to Pay Additional Fees for PCT/US2015/024297 dated Jun. 12, 2015.

(Continued)

*Primary Examiner* — Salil Jain
(74) *Attorney, Agent, or Firm* — Wolf, Greenfield & Sacks, P.C.

(57) ABSTRACT

Articles and methods for the active transport of molecules into, within, and/or from a matrix are generally described. In some embodiments, an electric field may be used to alter the position of the molecule with respect to the matrix. The electric field may be used to move the molecule to a new location within the matrix, remove the molecule from the matrix, or infuse the molecule into the matrix. For instance, the electric field may be used to move a molecule having a binding partner within the matrix into or away from the vicinity of the binding partner. In some embodiments, the position of the molecule may be altered by exposing the molecule to an electrodynamic field. In some such embodiments, the molecule exposed to the dynamic electric field may have enhanced mobility and minimal adverse matrix interactions relative to conventional molecular transport methods, and in some cases, a molecule exposed to an electrostatic field. The active transport methods and articles, described herein, may be particularly well-suited for a (Continued)

variety of applications including histological, biological, and pharmaceutical applications.

18 Claims, 11 Drawing Sheets

(58) Field of Classification Search
CPC ............... C07K 1/285; B01L 2200/10; B01L 2400/0421; G02F 1/167
See application file for complete search history.

(56) References Cited

U.S. PATENT DOCUMENTS

| | | | |
|---|---|---|---|
| 4,278,701 A | 7/1981 | von Hagens | |
| 4,320,157 A | 3/1982 | von Hagens | |
| 4,479,861 A * | 10/1984 | Hediger | B01D 57/02 204/615 |
| 4,707,233 A * | 11/1987 | Margolis | B01D 57/02 204/462 |
| 4,784,873 A | 11/1988 | Kienecker et al. | |
| 4,886,589 A * | 12/1989 | Southern | G01N 27/44773 204/458 |
| 5,041,203 A * | 8/1991 | Serwer | G01N 27/44773 204/457 |
| 5,089,288 A | 2/1992 | Berger | |
| 5,095,217 A | 3/1992 | Attix | |
| 5,131,994 A | 7/1992 | Shmidt et al. | |
| 5,279,721 A * | 1/1994 | Schmid | G01N 27/44717 204/457 |
| 5,356,771 A | 10/1994 | O'Dell | |
| 5,431,952 A | 7/1995 | Ocello | |
| 6,042,874 A | 3/2000 | Visinoni et al. | |
| 6,207,408 B1 | 3/2001 | Essenfeld et al. | |
| 6,379,921 B1 | 4/2002 | Pajak | |
| 6,586,713 B2 | 7/2003 | Essenfeld et al. | |
| 6,793,890 B2 | 9/2004 | Morales et al. | |
| 6,881,435 B2 | 4/2005 | Klosowski et al. | |
| 7,470,401 B2 | 12/2008 | Morales | |
| 7,547,538 B2 | 6/2009 | Morales et al. | |
| 7,569,342 B2 | 8/2009 | Baker | |
| 8,221,996 B2 | 7/2012 | Morales et al. | |
| 8,288,168 B2 | 10/2012 | Morales | |
| 2001/0052462 A1 | 12/2001 | Ogle et al. | |
| 2004/0259377 A1 | 12/2004 | Tupper et al. | |
| 2007/0151853 A1* | 7/2007 | Beardslee | C07K 1/26 204/456 |
| 2007/0284250 A1* | 12/2007 | Magnant | G01N 27/44739 204/459 |
| 2008/0083621 A1* | 4/2008 | Sideris | G01N 27/44713 204/450 |
| 2008/0164149 A1* | 7/2008 | Artz | G01N 27/44708 204/607 |
| 2010/0294665 A1 | 11/2010 | Allen et al. | |
| 2011/0220501 A1* | 9/2011 | Witkowski | G01N 27/44713 204/457 |
| 2012/0135541 A1* | 5/2012 | Herr | G01N 27/44791 436/501 |
| 2013/0143323 A1 | 6/2013 | Frost et al. | |
| 2014/0048417 A1 | 2/2014 | Heller et al. | |

FOREIGN PATENT DOCUMENTS

| | | |
|---|---|---|
| GB | 2177211 A | 1/1987 |
| WO | WO 87/02133 A1 | 4/1987 |
| WO | WO 00/035275 A1 | 6/2000 |
| WO | WO 2004/104557 A2 | 12/2004 |
| WO | WO 2010/126897 A1 | 11/2010 |
| WO | WO 2012/074468 A1 | 6/2012 |
| WO | WO 2014/025392 A1 | 2/2014 |

OTHER PUBLICATIONS

International Search Report and Written Opinion for PCT/US2015/024297 dated Aug. 20, 2015.
International Preliminary Report on Patentability dated Oct. 13, 2016 for Application No. PCT/US2015/024297.
EP 15773329.6, Dec. 22, 2017, Extended European Search Report.
Extended European Search Report dated Dec. 22, 2017 for Application No. EP 15773329.6.
Kim et al., Stochastic electrotransport selectively enhances the transport of highly electromobile molecules. Proc Natl Acad Sci. 2015;112(46):E6274-83. Supporting Information, 33 pages. E pub Nov. 2, 2015.
Chung et al., Structural and molecular interrogation of intact biological systems. Nature. May 16, 2013;497:332-339.
Chung et al., CLARITY for mapping the nervous system. Nature Methods. Jun. 2013;10(6):508-513. Epub May 30, 2013.
Dodt et al., Ultramicroscopy: three-dimensional visualization of neuronal networks in the whole mouse brain. Nat. Methods. Apr. 2007; 4(4):331-6. Epub Mar. 25, 2007.
Dunn et al., Methods in Molecular Biology, vol. 32: Basic Protein and Peptide Protocols. Ch. 12: Two Dimensional Polyacrylamide Gel Electrophoresis Using Immobilized pH Gradients in the First Dimension, pp. 87-96, Humana Press, Inc., Totowa, NJ, 1994.
Erturk et al., Three-dimensional imaging of solvent-cleared organs using 3DISCO. Nat. Protoc. 2012;7(11):1983-95.
Gleave et al., A Method for 3D Immunostaining and Optical Imaging of the Mouse Brain Demonstrated in Neural Progenitor Cells. PLoS ONE. Aug. 2013;8(8):e72039(1-12).
Hama et al., Sca/e: a chemical approach for fluorescence imaging and reconstruction of transparent mouse brain. Nat. Neurosci. Nov. 2011;14(11):1481-8.
Jahrling et al., 3D-reconstruction of blood vessels by ultramicroscopy. Organogenesis 2009;5(4):227-30. Epub Oct. 1, 2009.
Ke et al., SeeDB: a simple and morphology-preserving optical clearing agent for neuronal circuit reconstruction. Nat. Neurosci. Aug. 2013;16(8):1154-61. Epub Jun. 23, 2013.
Kim et al., Light microscopy mapping of connections in the intact brain. Trends Cogn. Sci. Dec. 2013;17(12):596-9.
Kuwajima et al., ClearT: a detergent- and solvent-free clearing method for neuronal and non-neuronal tissue. Development. 2013;140:1364-8.
Liu et al., A novel protocol of whole mount electro-immunofluorescence staining. Mol. Vis. 2009;15:505-17. Epub Mar. 6, 2009.
Renier et al., iDISCO: A simple, rapid method to immunolabel large tissue samples for volume imaging. Cell. Nov. 6, 2014;159:896-910.
Susaki et al,. Whole-brain imaging with single-cell resolution using chemical cocktails and computational analysis. Cell. Apr. 24, 2014; 157:726-39.
Tomer et al., Advanced CLARITY for rapid and high-resolution imaging of intact tissues. Nat. Protoc. Jul. 2014;9:1682-97, author manuscript, 33 pages.
Vakoc et al., Three-dimensional microscopy of the tumor microenvironment in vivo using optical frequency domain imaging. Nat. Med. Oct. 2009;15(10):1219-23.
Yang et al., Single-cell phenotyping within transparent intact tissue through whole-body clearing. Cell. Aug. 14, 2014;158:945-58.

* cited by examiner

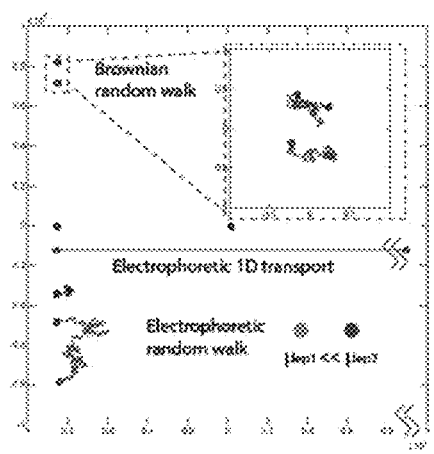
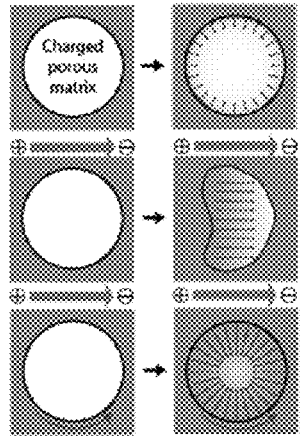
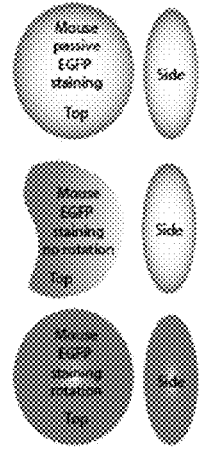
FIG. 8A　　　　　FIG. 8B　　　　　FIG. 8C
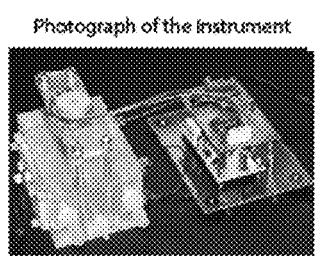
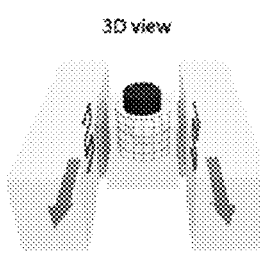
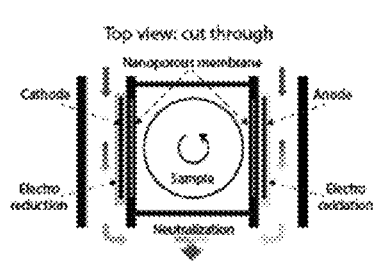
FIG. 8D　　　　　FIG. 8E　　　　　FIG. 8F

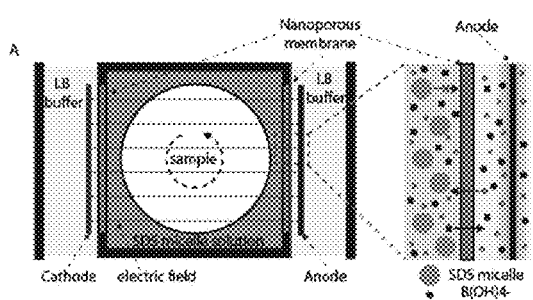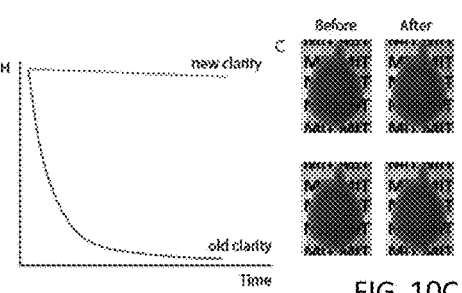
FIG. 10A  FIG. 10B  FIG. 10C
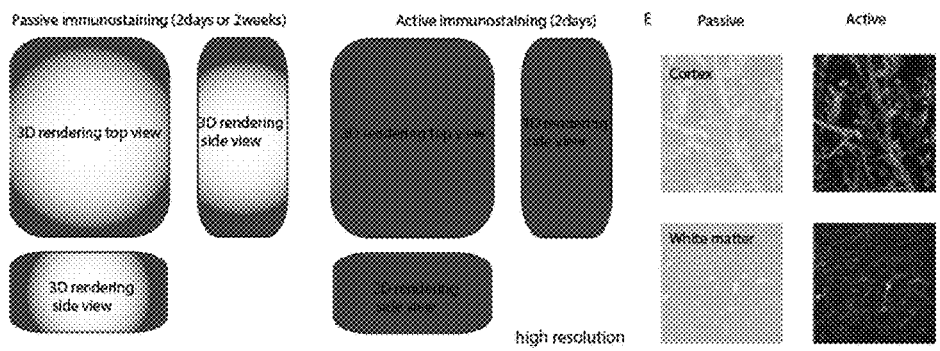
FIG. 10D  FIG. 10E
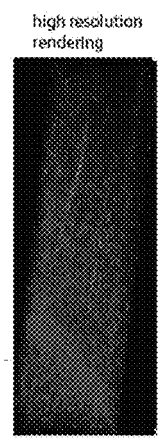
FIG. 10F
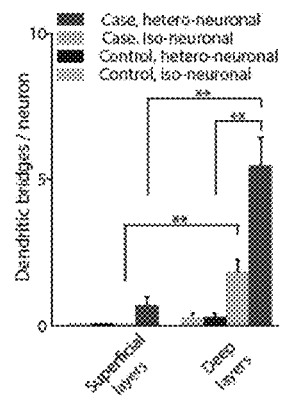
FIG. 10G

ACTIVE TRANSPORT OF CHARGED MOLECULES INTO, WITHIN, AND/OR FROM CHARGED MATRICES

RELATED APPLICATIONS

This application claims the benefit of U.S. Provisional Patent Application Ser. No. 61/975,575, filed Apr. 4, 2014, entitled "Active Transport of Charged Molecules, into, Within, and/or from Charged Matrices," which is incorporated herein by reference in its entirety.

TECHNICAL FIELD

Articles and methods for the active transport of molecules into, within, and/or from matrices, including biological matrices, are provided.

BACKGROUND

The transport of molecules is fundamental to life as well as many engineered systems. Transport processes may be passive or active. One example of passive transport is diffusion. Diffusion is the process by which molecules move from regions of high concentration to regions of low concentration. In diffusion, the molecules move via Brownian motion and undergo a random walk that results in a net displacement of the molecules in the direction of lower concentration. Active transport processes utilize energy to move molecules. In some active transport processes, a force is applied to the system comprising the molecules, such that the molecules move in the direction of the force. Though molecules may be transported via passive or active means, the active transport of molecules is advantageous for many applications. Accordingly, improved articles and methods for the active transport of molecules are needed.

SUMMARY

Articles and methods for the active transport of molecules into, within, and/or from matrices are provided. The subject matter of the present invention involves, in some cases, interrelated products, alternative solutions to a particular problem, and/or a plurality of different uses of one or more systems and/or articles.

In one set of embodiments, articles are provided. In one embodiment, an article comprises an electric field generator, a chamber capable of being positioned in a field provided by the generator, wherein at least a portion of the chamber is defined by a semipermeable material, and a sample positioner in the chamber.

In another set of embodiments, methods are provided. In one embodiment, a method comprises driving a molecule through at least a portion of a matrix using an electrodynamic field.

In another embodiment, a method comprises driving molecules through at least a portion of a charged matrix, using an electric field, thereby changing the concentration of the molecules in at least about 10% of the matrix, while deforming the matrix in an amount less than 10%.

In one embodiment, a method comprises exposing a molecule to an electric field in the presence of a matrix and associating the molecule with a binding partner within the matrix.

In another embodiment, a method comprises distributing molecules throughout a matrix using an electric field, wherein the variation in concentration of the molecules throughout the matrix is less than 25%.

In one embodiment, a method comprises distributing molecules throughout a matrix comprising binding partners for the molecules under a condition that inhibits binding between at least a portion of the molecules and the binding partners.

In another embodiment, a method comprises driving a molecule through a charged matrix using an electric field having a magnitude greater than or equal to 10 V/m.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 8A illustrates methods and articles for electrophoretic random walk, according to certain embodiments;

FIG. 8B illustrates methods and articles for electrophoretic random walk, according to certain embodiments;

FIG. 8C illustrates methods and articles for electrophoretic random walk, according to certain embodiments;

FIG. 8D illustrates methods and articles for electrophoretic random walk, according to certain embodiments;

FIG. 8E illustrates methods and articles for electrophoretic random walk, according to certain embodiments;

FIG. 8F illustrates methods and articles for electrophoretic random walk, according to certain embodiments;

FIG. 10A illustrates the active transport of immonostaining molecules into brain tissue, according to one set of embodiments;

FIG. 10B illustrates the active transport of immonostaining molecules into brain tissue, according to one set of embodiments;

FIG. 10C illustrates the active transport of immonostaining molecules into brain tissue, according to one set of embodiments;

FIG. 10D illustrates the active transport of immonostaining molecules into brain tissue, according to one set of embodiments;

FIG. 10E illustrates the immunostaining of thick brain samples, according to one set of embodiments;

FIG. 10F illustrates the immunostaining of thick brain samples, according to one set of embodiments;

FIG. 10G illustrates the immunostaining of thick brain samples, according to one set of embodiments;

DETAILED DESCRIPTION

Articles and methods for the active transport of molecules into, within, and/or from a matrix are generally described. In some embodiments, an electric field may be used to alter the position of the molecule with respect to the matrix. The electric field may be used to move the molecule to a new location within the matrix, remove the molecule from the matrix, or infuse the molecule into the matrix. For instance, the electric field may be used to move a molecule having a binding partner within the matrix into or away from the vicinity of the binding partner. In some embodiments, the position of the molecule may be altered by exposing the molecule to an electrodynamic field. In some such embodiments, the molecule exposed to the dynamic electric field may have enhanced mobility and minimal adverse matrix interactions relative to conventional molecular transport methods, and in some cases, a molecule exposed to an electrostatic field. The active transport methods and articles, described herein, may be particularly well-suited for a variety of applications including histological, biological, and pharmaceutical applications.

Figure 1A:
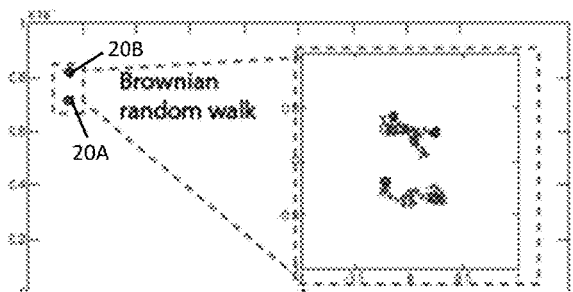
FIG. 1A illustrates Brownian motion of molecules in the presence of a matrix, according to certain embodiments.
Figure 1B:
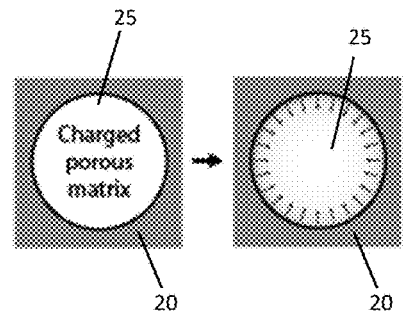
FIG. 1B illustrates passive transport of molecules into a matrix via diffusion, according to certain embodiments.

Numerous applications in science and technology require the transport of molecules into, within, or from a matrix. Conventional methods for positioning molecules with respect to a matrix often rely on passive transport methods, such as diffusion. However, the passive transport of molecules can be relatively slow and, for many applications, the desired arrangement of molecules with respect to the matrix cannot be achieved within the requisite timeframe using passive transport methods. An example of passive transport is shown in FIGS. 1A-1B. FIG. 1A illustrates the diffusion of molecules 20 (e.g., 20A and 20B) into a matrix. Since the movement of molecules via diffusion is based on collisions, the molecules make small random movements and the net displacement of both molecules is relatively small. Accordingly, as shown in FIG. 1B, the penetration of the molecules 20 into the matrix 25 over time is relatively minimal and the molecules accumulate at the surface of the matrix.

An alternative to passive transport is active transport. Conventional active transport methods generally rely on the application of a force (e.g., hydrodynamic force) to the system containing the molecules and the matrix. The force may cause the molecules to migrate in the direction of the force, such that the net displacement of the molecule in the direction of the force is proportional to the magnitude of the force. Still, many conventional active transport systems are limited by the magnitude of the force capable of being generated and/or the effect of the force on the molecules and/or matrix. For instance, in some embodiment, a force above a certain threshold and/or exposure of the matrix to the force over an extended period of time may adversely affect the matrix.

It has been discovered, within the context of certain embodiments of the present invention, that rapid transport of molecules into, within, and/or from a matrix can be achieved without adversely affecting the molecules and/or matrix using an electric field. In some embodiments, the electric field may be applied to molecules in a manner that induces non-traditional electrophoretic movement such that the net displacement of the molecule is enhanced relative to certain conventional techniques. Without being bound by theory, it is believed that, in certain embodiments, the articles and methods, described herein, can be used to induce molecular movement via an electrophoretic random walk that mimics Brownian motion but results in a relatively large net displacement of the molecules.

Figure 2A:
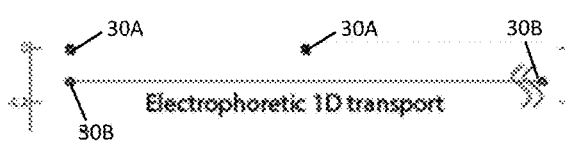
FIG. 2A illustrates active transport in the presence of a matrix using an electric field, according to one set of embodiments.
Figure 2B:
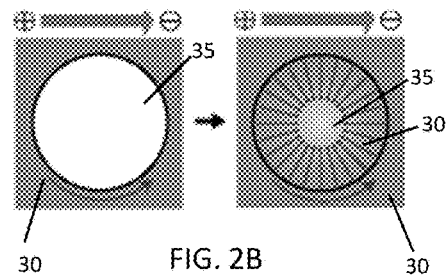
FIG. 2B illustrates active transport of molecules into a matrix via electrophoretic linear motion, according to one set of embodiments.

Examples of active transport of molecules using an electric field, as described herein, are shown in FIGS. 2-4. In some embodiments, charged molecules 30 (e.g., 30A and 30B) may be exposed to an electrostatic field as shown in FIGS. 2A-2B. The electrostatic field experienced by the charged molecules 30 (e.g., 30A and 30B) may induce electrophoretic movement of the molecules in the direction of the electrostatic field. In the electric field, molecule 30B with a higher charge density may move faster than molecule 30A with a smaller charge density as illustrated in FIG. 2A. In some such embodiments, the electrostatic field may be 1-dimensional and the charged molecules may move linearly in the direction of the electrostatic field as illustrated in FIGS. 2A-2B. As illustrated in FIG. 2B, in certain embodiments, the molecules 30 can be rapidly distributed within the matrix 35 in the direction of the field, as indicated by the arrows, without adversely affect the molecules and/or matrix and the molecules. In some such embodiments, the molecules may be distributed throughout the matrix relatively evenly. For example, the molecules may be distributed throughout the matrix such that the variation in the concentration of the molecules throughout the matrix is less than or equal to about 25% (e.g., less than or equal to about 20%, less than or equal to about 15%, less than or equal to about 10%, less than or equal to about 5%). In another example, an electric field can be used to drive molecules through a least a portion of a charged matrix, such that the concentration of the molecules in the matrix changes by at least about 10% (e.g., at least about 75%), but the change in a cross-sectional dimension or any other deformation of the matrix is less than 10%. In some embodiments, active transport of molecules into, within, and/or from a matrix using a static electric field may be well-suited for uncharged matrices and matrices having a relatively low charge density, amongst other matrices.

Figure 3A:
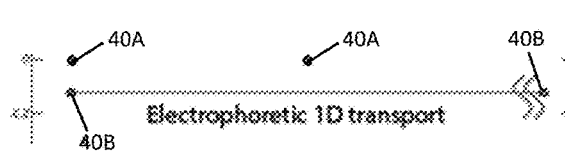
FIG. 3A illustrates active transport in the presence of a matrix using an electric field, according to certain embodiments.
Figure 3B:
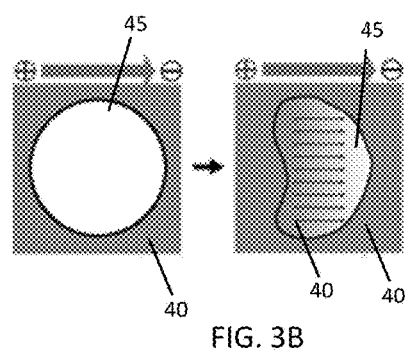
FIG. 3B illustrates active transport of molecules into a matrix via electrophoretic linear motion, according to certain embodiments.

In other embodiments, as illustrated in FIG. 3A, a matrix 45 (e.g., biological system) may have a relatively high charge density, such that the electrostatic field experienced by the matrix induces electrophoretic movement of the molecules 40 (e.g., 40A and 40B), as shown in FIG. 3A, and of the matrix 45, as shown in FIG. 3B. In certain embodiments, the electrophoretic movement of the charged matrix may be substantially slower than the electrophoretic movement of the charged molecules, such that at least a portion of the molecules are driven into the highly charged matrix. In some embodiments, the continual exposure of the highly charged matrix to an electrostatic field may cause a cross-sectional dimension of the matrix to be altered and/or otherwise deform the matrix, as illustrated in FIG. 3B. In some embodiments, non-traditional electrophoretic methods and articles may be used to move molecules into, within, and/or from the matrix without adversely affect the molecules and/or matrix and the molecules.

Figure 4A:
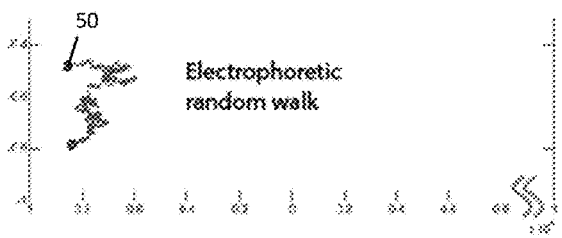
FIG. 4A illustrates active transport in the presence of a matrix using an electric field, according to one set of embodiments.
Figure 4B:
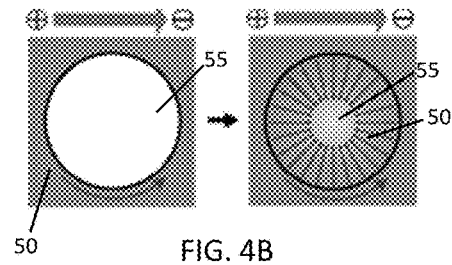
FIG. 4B illustrates active transport of molecules into a matrix via electrophoretic random walk, according to one set of embodiments.

In some embodiments, molecules may be driven through at least a portion of a matrix (e.g., highly charged matrix) without adversely affecting the molecules and/or matrix using an electrodynamic field, as illustrated in FIG. 4B. For instance, a matrix 55 with a high charged density may be exposed to an electric field that has at least one dynamic property (e.g., direction and/or magnitude change as function of time). In some such embodiments, the charged matrix can avoid the effects of being subjected to a continual and substantial force in a single direction due to the electric field and/or flux of charged molecules. The reduction in the stress on the matrix substantially reduces the deformation of the matrix. This can be the case, for example, where the charged matrix is displaced by an applied field but, because of its interconnectivity, the matrix is not displaced as much as relatively unattached molecules within the matrix. When the electric field is changed relative to the matrix (e.g., the orientation of the field changes), molecules often are driven more extensively than the more interconnected matrix. The net effect, over time, is that the molecules migrate significantly more extensively than the matrix (at times throughout the entire matrix), while the matrix experiences much less overall net movement, at times essentially no net movement. For example, an electrodynamic field can be used to drive molecules through a least a portion of a relatively highly charged matrix, such that the concentration of the molecules in the matrix changes by at least about 10% (at least about at 75%), but the change in the cross-sectional dimension of the matrix is less than or equal to about 10% (e.g., less than or equal to about 3%).

In some embodiments, the electrodynamic field may cause the molecules 50 to undergo an electrophoretic random walk as illustrated in FIG. 4A. The electrophoretic random walk can be caused, at least in part, by the fact that as the orientation of the electric field changes relative to the matrix, charged molecules in the matrix are urged in different directions. This, coupled with an inherent stochastic pathway that can exist within some matrices (analogous to channels in a foam including voids and more rigid regions) results in a semi-random or stochastic, non-linear, changing, potentially tortuous pathway of movement undertaken by the molecules. Without being bound by theory, it is believed that the net displacement of molecules moving via electrophoretic random walk is proportional to the quadratic of the magnitude of the product of electromobility and the electric field, whereas electrophoretic linear movement is linearly proportional to the magnitude of the product of the electromobility and the electric field. This quadratic dependence selectively boosts migration of only freely moving charged molecules with high electromobility while suppressing movement of a charged matrix with low electromobility. For example, in an embodiment in which a free charged molecule has a three orders of magnitude higher electromobility than a molecule tethered to the matrix, under a condition that would induce a 1 mm displacement of the charged molecule, the tethered molecule would move only 1 nm in an electrodynamic field (e.g., via electrophoretic random walk) and 1 μm in an electrostatic field (e.g., via electrophoretic linear motion). Therefore, it is believed that an electrodynamic field may be used to increase the rate of transport of molecules into, within, or from a matrix.

As used herein, the terms "electrostatic field" and "static electric field" have their ordinary meaning in the art and may refer to a non-zero electric field that does not change as a function of time. Conversely, the terms "electrodynamic field" and "dynamic electric field" have their ordinary meaning in the art and may refer to an electric field that has at least one property that changes as a function of time. Commonly, the property may be the electric field magnitude, the direction of the electric field, the electric field frequency, or movement of the matrix in a stationary electric field, or two or more properties simultaneously, although there are other variable features of electric fields that can result in an electrodynamic field. In some embodiments, the shape of the electric field may be altered to produce an electrodynamic field. The electric field can be "shaped" in a manner that allows the electric field to be "focused" to a region of interest. For example, the shape of the electric field could be manipulated, such that the electric potential difference across a certain small region of interest is larger compared to other surroundings regions within the electric field. In general, any suitable variance of one or more property of the electrodynamic field may be used, provided that the electric field experienced by the matrix is dynamic. In some instances, the variance in one or more property of the electrodynamic field may be regular, irregular, and/or stochastic. In embodiments in which more than one property varies as a function of time, the variance for two or more properties may be the same or different. In some arrangements, contribution to the variability of an electrodynamic field can include reductions in the magnitude of the field to zero, or near zero, for one or more periods of time.

It should also be understood that, as used herein, the terms "electrostatic" and "electrodynamic" field refer to the field experienced by the matrix at most or all of the points in time when the field is applied. For example, a regular oscillating heterogeneous matrix positioned between two stationary and oppositely charged point charges would be referred to as being in an electrodynamic field and molecules would be transported using an electrodynamic field. As another example, an electrodynamic field may be applied to a matrix, whose movements are coupled with the dynamic property of the electric field, such that at all points in time the relative position of the matrix to the electric field to remains the same. The matrix would be referred to as being in an electrostatic field and molecules would be transported using an electrostatic field. In another example, a stationary matrix in an electrostatic field provided by an electric field generator would be referred to as being in an electrostatic field and molecules would be transported using an electrostatic field. In some embodiments, articles, as described herein, may be configured to produce a dynamic or static electric field.

Figure 5A:
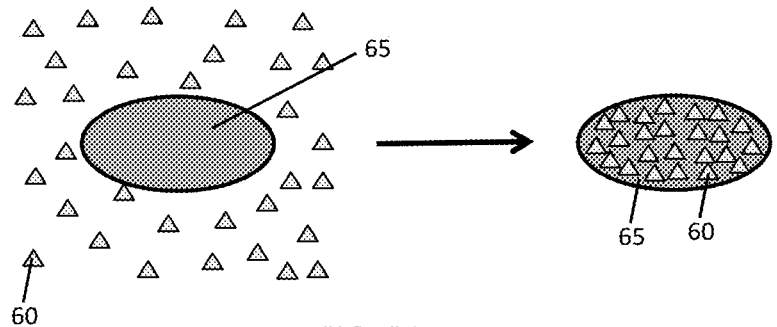
FIG. 5A illustrates the infusion of molecules into a matrix, according to certain embodiments.
Figure 5B:
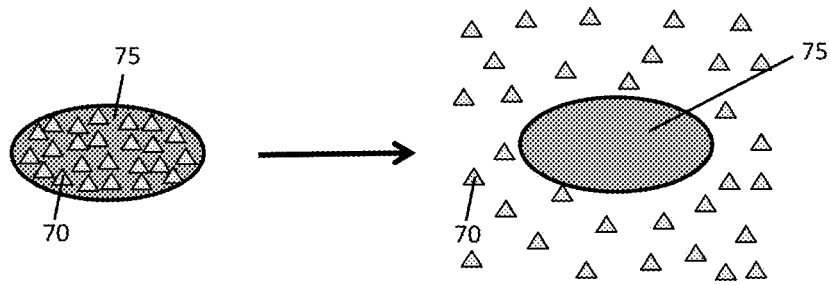
FIG. 5B illustrates removal of molecules from a matrix, according to certain embodiments.
Figure 5C:
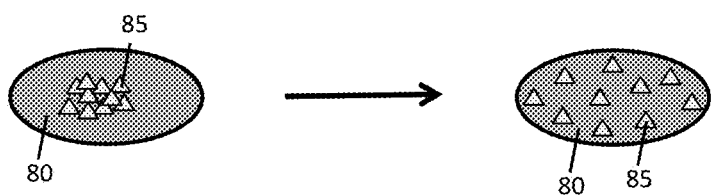
FIG. 5C illustrates distribution of molecules within a matrix using an electric field, according to certain embodiments.

Non-limiting examples of driving a molecule through at least a portion of a matrix are shown in FIGS. 5A-5C. In some embodiments, as illustrated in FIG. 5A, molecules 60 may be in the presence of a matrix 65. In some embodiments, at least a portion of the molecules may be outside of the matrix. An electric field (e.g., static, dynamic), as described herein, may be applied to the region comprising the molecules and the matrix. The electric field may cause at least a portion of the molecule to infuse into at least a portion of the matrix as indicated by the arrow. In some instances, the molecules may be distributed relatively evenly throughout the matrix as shown in FIG. 5A. For example, the variation in concentration of the molecules throughout the matrix may be less than or equal to about 25% (e.g., less than or equal to about 20%, less than or equal to about 15%, less than or equal to about 10%, less than or equal to about 5%, less than or equal to about 3%, less than or equal to about 2%, less than or equal to about 1%).

In some embodiments, as illustrated in FIG. 5B, molecules 70 may be within a matrix 75. An electric field (e.g., static, dynamic), as described herein, may be applied to the region comprising the molecules and the matrix. The electric field may cause at least a portion of the molecule to be removed from at least a portion of the matrix as indicated by the arrow. In certain embodiments, the electric field may cause a large percentage of the molecules to be removed from the matrix. For instance, in some embodiments, an electric field can be used to remove at least about 50% (e.g., at least about 60%, at least about 70%, at least about 75%, at least about 80%, at least about 85%, at least about 90%, at least about 95%) of a desired charged molecule from a matrix (e.g., charged matrix). In certain embodiments, substantially all of the molecules may be removed from the matrix as show in FIG. 5B.

In some embodiments, a matrix 85 may comprise molecules 80 that are unevenly distributed within the matrix, as illustrated in FIG. 5C. In some instances, the molecules may be concentrated at one or more locations within the matrix, such that there is a relatively large variation in the concentration of the molecule throughout the matrix. In some such embodiments, the concentration of the molecule throughout the matrix may be relatively inhomogeneous, such that significant concentration gradients exist between different regions within the matrix. For example, the molecules may be concentrated at a location in the interior of the matrix, such that concentration of the molecule at that location is relatively high and the concentration of the molecule at other location in the matrix (e.g., near the surface) is relatively low or zero. In some embodiments, as illustrated in FIG. 5C, an electric field (e.g., static, dynamic), as described herein, may be applied to the region comprising the molecules and the matrix. The electric field may cause the molecules to distribute throughout the matrix, such that the variation in concentration of the molecules throughout the matrix is reduced and/or relatively low. For example, the variation in concentration of the molecules throughout the matrix may be less than or equal to about 25% (e.g., less than or equal to about 20%, less than or equal to about 15%, less than or equal to about 10%, less than or equal to about 5%, less than or equal to about 3%, less than or equal to about 2%, less than or equal to about 1%).

In general, the methods and articles, described herein, may be used to change the concentration of a molecule in a matrix as illustrated in FIG. 5. In some embodiments, the methods and articles, described herein, may be used to change the concentration of the molecule in at least about 10% (e.g., at least about 20%, at least about 30%, at least about 40%, at least about 50%, at least about 60%, at least about 70%, at least about 80%, at least about 90%, at least about 95%, at least about 97%) of the matrix. In some embodiments, the methods and articles, described herein, may be used to change the concentration of the molecule in a relatively large percentage of the matrix, e.g., at least about 75%, at least about 80%, at least about 85%, at least about 90%, or at least about 95%. In some embodiments, large changes in concentration may occur when the methods and articles, described herein, are used to infuse and or remove molecules into or from, respectively, a matrix.

In certain embodiments, the methods and articles, described herein, may be used to change the concentration of the molecule in a small percentage of the matrix, e.g., less than or equal to about 25%, less than or equal to about 20%, less than or equal to about 15%, less than or equal to about 10%, or less than or equal to about 5%. In some embodiments, small changes in the concentration of the molecule may occur when the methods and articles, described herein, are used to rearrange or distribute molecules that are already within the matrix.

As described herein, in some embodiments, the molecules may be transported into, within, or from a matrix without adversely affecting the matrix. For example, a charged molecule may be moved into, within, or from a charged matrix without significantly altering one or more cross-sectional dimensions of the matrix or otherwise deforming the matrix. For instance, in some embodiment, the methods may alter one or more cross-sectional dimensions of the matrix or otherwise deforming the matrix in an amount less than about 15%, less than about 12%, less than about 10%, less than about 8%, less than about 5%, less than about 3%, less than about 2%, or less than about 1%. For example, a method may drive molecules through at least a portion of a charged matrix, using an electric field, thereby changing the concentration of the molecules in at least about 10% (e.g., at least about 75%) of the matrix, while deforming the matrix in an amount less than 10% (e.g., less than about 3%).

Figure 6A:
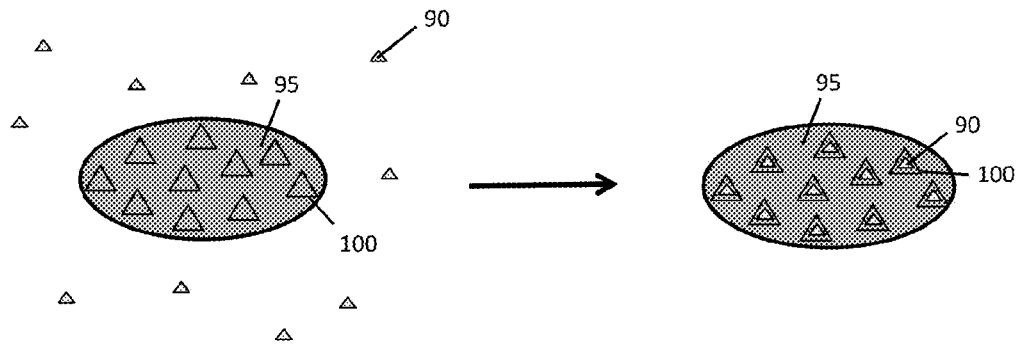
FIG. 6A illustrates the association of molecules with a matrix having binding partners for the molecule, according to one set of embodiments.

In some embodiments, the matrix may comprise one or more binding partners for one or more molecule to be transported. For instance, as illustrated in FIG. 6A, molecules 90 may be in the presence of a matrix 95 comprising binding partners 100 for the molecules. The region comprising the molecules and the matrix may be exposed to an electric field (e.g., static, dynamic), as described herein. The electric field may cause at least a portion of the molecule to infuse into at least a portion of the matrix and associate with the binding partner as indicated by the arrow.

Figure 6B:
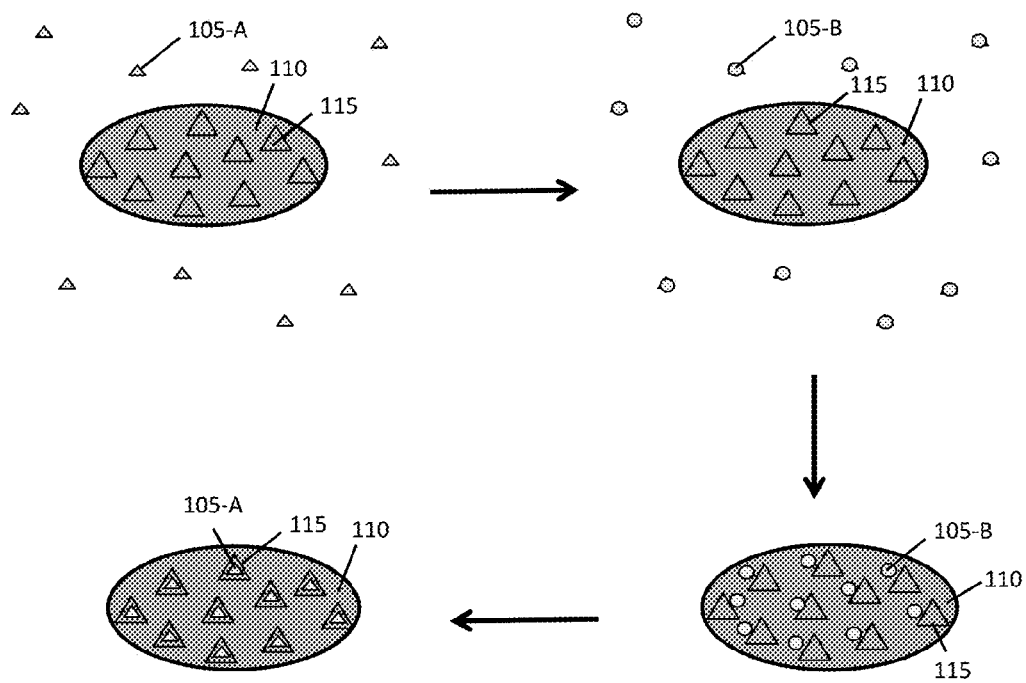
FIG. 6B illustrates the distribution and association of molecules within a matrix having binding partners for the molecule under certain conditions, according to one set of embodiments.

In some embodiments, prior to and/or while the molecule are being driven through (e.g., into, within, and/or from) at least a portion of the matrix, the molecules and/or matrix may be exposed to a condition that inhibits the association between the molecule and the binding partner. For example, as illustrated in FIG. 6B, the molecules and the matrix 110 may be exposed to a condition (e.g., pH, ionic concentration, concentration of a chemical species) that alters a property of the molecule (e.g., charge, molecular conformation) that inhibits the association between the molecule and the binding partner 115. FIG. 6B shows molecules 105-A having a property A prior to exposure to the condition and a property B, thus forming molecules 105-B, after exposure to the condition. The molecules 105-B may then be driven through at least a portion of the matrix. In some embodiments, inhibiting the association between the molecule and a binding partner during transport may enhance the rate of transport and/or facilitate the distribution of the molecule within the matrix. For example, in embodiments in which the total number of molecules is less than the total number of binding partners, molecules that are infused into the matrix may disproportionately associate with binding partners at or near the surface of the matrix. In some such embodiments, there may be a relatively large variation in the concentration of the molecule throughout the matrix.

As illustrated in FIG. 6B, exposing the molecules and/or matrix to a condition that inhibits the association between the molecule and a binding partner during transport may allow the molecule to distribute throughout the matrix such that the variation in concentration of the molecule throughout the matrix is relatively low (e.g., less than or equal to about 25%). After molecules 105-B have been distributed in the matrix, the molecules and/or matrix may be exposed to a condition that facilitates or does not inhibit the association between the molecules and the binding partners. In some such embodiments, molecules 105-B may form molecule 105-A, and associate with the binding partners. In certain embodiments, the condition that facilitates or does not inhibit association may, in some instances, enhances the ability of the molecule and binding partner to associate.

Figure 7:
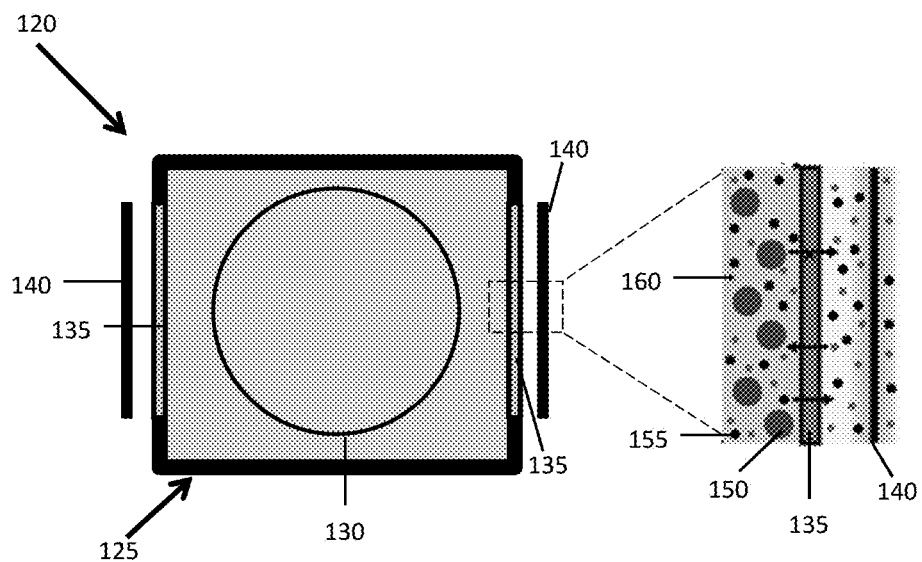
FIG. 7 illustrates an article for the electrophoretic movement of molecules, according to one set of embodiments.
Figures 9A, 9B:
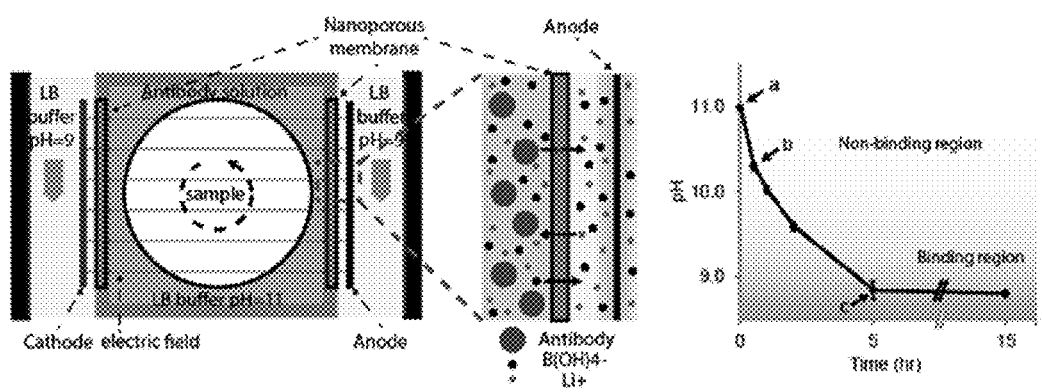
FIG. 9A illustrates methods and articles for electrophoretic random walk under a condition that inhibits or facilitates the association of molecules and binding partners, according to certain embodiments.
FIG. 9B illustrates methods and articles for electrophoretic random walk under a condition that inhibits or facilitates the association of molecules and binding partners, according to certain embodiments.
Figure 9C:
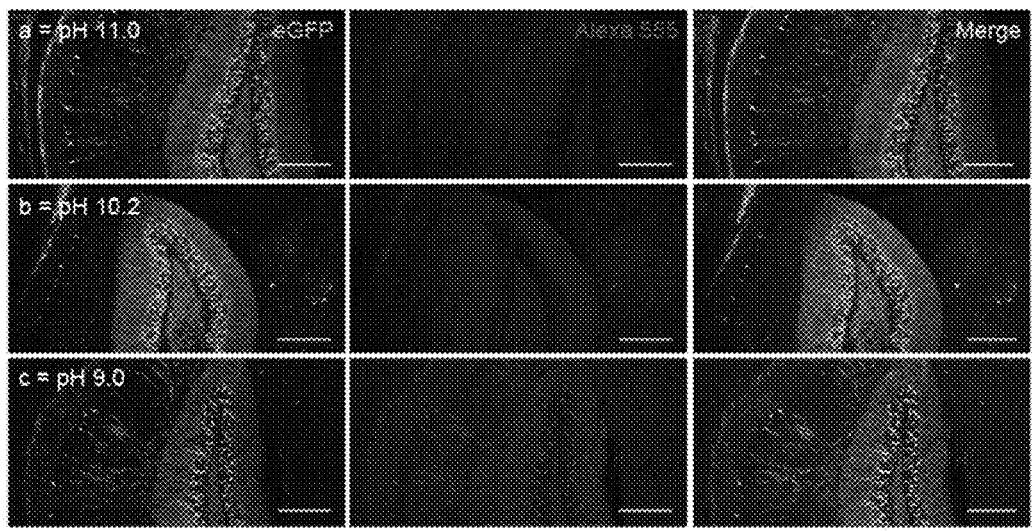
FIG. 9C illustrates methods and articles for electrophoretic random walk under a condition that inhibits or facilitates the association of molecules and binding partners, according to certain embodiments.
Figure 9D:
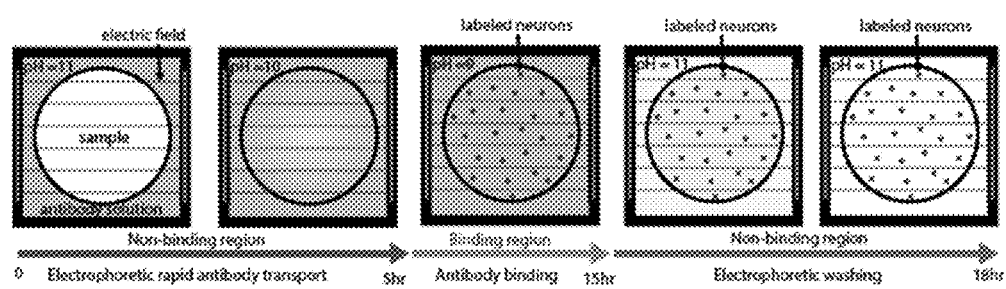
FIG. 9D illustrates methods and articles for electrophoretic random walk under a condition that inhibits or facilitates the association of molecules and binding partners, according to certain embodiments.
Figure 9E:
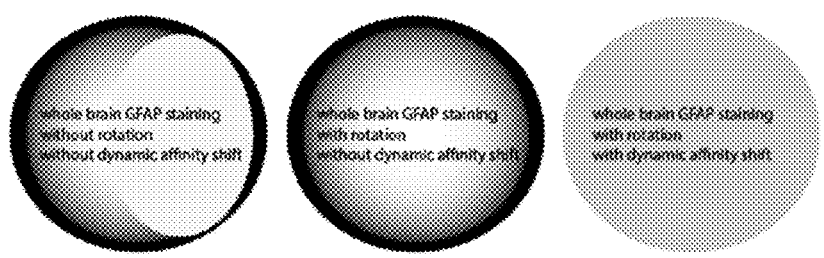
FIG. 9E illustrates methods and articles for electrophoretic random walk under a condition that inhibits or facilitates the association of molecules and binding partners, according to certain embodiments.

An example of an article 120 for the active transport of molecules using an electric field, as described herein, is shown in FIG. 7. In some embodiments, the article may comprise an electric field generator 140, a chamber 125, at least one semipermeable material 135, and a sample positioner 130 as illustrated in FIG. 7. The chamber may be capable of being positioned in a field provided by the electric field generator (e.g., two electrodes; an anode and a cathode) and at least a portion of the chamber is defined by a semipermeable material (e.g., porous material, nanoporous material) having a specific molecular weight cutoff (e.g., between about 50,000 and about 500,000 g/mol; between about 100,000 g/mol and about 500,000; between about 500 g/mol and about 10,000 g/mol).

In general, any suitable electric field generator capable of producing an electric field may be used. In some instances, the electric field generator may comprise two or more electrodes (e.g., an anode and a cathode), driven by a source of electromotive force from a power supply. In some embodiments the electric field generator may be capable of producing an electrostatic or electrodynamic field. Any suitable method of providing a static or dynamic electric field may be used. In some embodiments, an electrostatic field may be produced by applying a static potential difference between at least two electrodes that do not move relative to the matrix during the process. Electrodynamic fields can be produced in a number of ways. In one, the orientation of apparatus that produces the field can be changed relative to the matrix. For example, a set of electrodes used to generate the field can be moved relative to the matrix by rotation or other movement about the matrix or the like. The matrix can be moved, the electrodes can be moved, or both. Alternatively, not all electrodes need to be moved relative to the matrix, but movement of any electrode relative to the matrix typically will change the orientation of the field relative to the matrix. In another set of arrangements, electrodes might not move relative to the matrix, but polarity and or extent of charge applied to the electrodes can be varied. For example, a matrix might be surrounded by a number of electrodes each oriented differently relative to the matrix, and not changing in position relative to the matrix. Electromotive force applied to the electrodes can be changed in intensity over time to create a field that varies overtime, and polarity can change between electrodes such that the field moves in any of a variety of ways relative to the matrix. In yet another set of arrangements, an electrodynamic field may be produced by dynamically changing the resistance of the matrix or the fluid surrounding the matrix. For instance, a highly viscous liquid can be injected or air bubbles can be introduced between the electrodes to increase the resistance of the surrounding fluid, which effectively enhances current going through the matrix. With this description, those of ordinary skill the art will be able to readily determine variations in these techniques and/or make use for other techniques to create electrodynamic fields tailored for specific applications.

In general, the chamber may be any suitable vessel capable of being positioned between the electric field generator, having at least a portion defined by a semipermeable material, housing a sample positioner, and retaining a fluid. In certain embodiments, the chamber may be capable of being positioned in a field provided by the electric field generator. For example, as shown in FIG. 7, the chamber 125 is positioned between the electric field generator 140. In embodiments in which the electric field generator comprises electrodes, the chamber may be capable of being positioned between two of the electrodes (e.g., an anode and a cathode). In certain embodiments, the chamber may be mobile and can be moved into the field manually or via automatic control. In other instances, the chamber may be stationary and positioned such that the chamber is in the region in which the electric field generator provides electric fields.

In some embodiments, at least a portion of the chamber is defined by a semipermeable material. The semipermeable material may be a selectively permeable membrane. In some embodiments, the semi-permeable material may allow certain molecules to be retained in the chamber while allowing other molecules to exit the chamber. In some such embodiments, retention of a desired molecule in the chamber may minimize the amount of molecule needed to achieve the desired outcome for a given application. For instance, retention of molecules used for staining the matrix may minimize the amount of staining molecules required to stain the matrix. In some embodiments, retention of certain molecules may allow the molecules to evenly distribute within the chamber and/or prevent the molecules from interacting with the electric field generator. In some embodiments, semipermeable material 135 may have a certain molecular weight cutoff and/or size cutoff, such that the semipermeable material is substantially impermeable to molecules at or above the molecular weight and/or size cutoff. For instance, as illustrated in the inset of FIG. 7, a semipermeable material 135 may be substantially impermeable to molecules 150, but permeable to other molecules (e.g., 155 and 160) that have a smaller molecular weight and/or size. In some embodiments, the semipermeable material may be porous. For example, the semipermeable material may be a nanoporous material.

As used herein, the term "molecular weight cutoff" has its ordinary meaning in the art and may refer to the lowest molecular weight of a molecule at which greater than 90% of the molecule is retained by the semipermeable material or greater than 99% of the molecule is retained by the semipermeable material. One of ordinary skill in the art would be aware that the ability of a semipermeable material to retain a molecule is also dependent on the shape of the molecule, such that in some cases a molecule having the requisite molecular weight may not be retained due to its shape. For instance a linear molecule having the requisite molecular weight may not be retained while a globular molecule having the same molecular weight is retained. The term "size cutoff" has its ordinary meaning in the art and may refer to lowest size of a molecule at which greater than 90% of the molecule is retained by the semipermeable material or greater than 99% of the molecule is retained by the semipermeable material. The size of the molecule may be defined by the molecular weight of the molecule or a cross-sectional dimension of a molecule (e.g., globular molecule).

In general, the molecular weight and/or size cutoff may be selected based on one or more property of the molecule(s) to be retained. For instance, a semipermeable material with a relatively high molecular weight and/or size cutoff (e.g., between about 50,000 g/mol and about 500,000 g/mol; between about 100,000 g/mol and about 500,000 g/mol) may be used to retain molecules having a high molecular weight, such as antibodies. In other instances, a semipermeable material with a relatively low molecular weight and/or size cutoff (e.g., between about 500 g/mol and about 10,000 g/mol; between about 500 g/mol and about 5,000 g/mol; between about 500 g/mol and about 3,000 g/mol) may be used to retain molecules having a low molecular weight, such as peptides, small molecules, oligomers, primers, etc. In some embodiments, the semipermeable material may have a molecular weight cutoff of about 500,000 g/mol, about 350,000 g/mol, about 200,000 g/mol, about 100,000 g/mol, about 75,000 g/mol, about 50,000 g/mol, about 25,000 g/mol, about 10,000 g/mol, about 5,000 g/mol, about 3,000 g/mol, about 2,000 g/mol, about 1,000 g/mol, or about 500 g/mol. In certain embodiments, the molecular weight cutoff may be between about 500 g/mol and about 500,000 g/mol, about 1,000 g/mol and about 500,000 g/mol, about 10,000 g/mol and about 500,000 g/mol, about 50,000 g/mol and about 500,000 g/mol, about 100,000 g/mol and about 500,000 g/mol, about 500 g/mol and about 50,000 g/mol, about 500 g/mol and about 10,000 g/mol, about 500 g/mol and about 5,000 g/mol, about 1,000 g/mol and about 50,000 g/mol, or about 1,000 g/mol and about 10,000 g/mol. In some embodiments, the semipermeable material may have a size cutoff of about 10 microns, about 5 microns, about 3 microns, about 2 microns, about 1 micron, about 0.8 microns, about 0.6 microns, about 0.5 microns, about 0.3 microns, about 0.2 microns, about 0.1 microns, about 0.05 microns, about 0.01 microns, about 0.005 microns, about 0.001 microns, or about 0.0005 microns. In some embodiments, the size cutoff may be between about 0.001 microns and about 10 microns, about 0.001 microns and about 5 microns, about 0.001 microns and about 1 micron, about 0.001 microns and about 0.5 microns, about 0.001 microns and about 0.1 microns, about 0.1 microns and about 10 microns, about 0.1 microns and about 10 microns, or about 1 micron and about 10 microns.

In some embodiments, the average pore size of the semipermeable material may be less than or equal to about 5 microns, less than or equal to about 3 microns, less than or equal to about 2 microns, less than or equal to about 1 micron, less than or equal to about 0.8 microns, less than or equal to about 0.6 microns, less than or equal to about 0.5 microns, less than or equal to about 0.3 microns, less than or equal to about 0.2 microns, less than or equal to about 0.1 microns, less than or equal to about 0.05 microns, less than or equal to about 0.02 microns, less than or equal to about 0.01 microns, or less than or equal to about 0.005 microns and greater than zero.

In some embodiments, the article for active transport of molecules using an electric field may also comprise a sample positioner. The sample positioner may be configured to hold a matrix (e.g., biological system). In some embodiments, the sample positioner may also be configured to move within the chamber. The matrix may be sufficiently secured to the sample positioner such that the matrix moves with the sample positioner. In certain embodiments, the sample positioner may be capable of oscillating and/or moving along a defined path. In some embodiments, the movement of the sample positioner may be used to form an electrodynamic field. For example, a matrix (e.g., biological system) may be positioned on a sample positioner and the sample positioner may be rotated, such that the matrix experiences an electrodynamic field. In general, the sample positioner may be configured to produce any suitable movement for the formation of static or dynamic electric fields. For instance, in some embodiments, the sample positioner may move continuously or periodically. In some embodiments, the positioner may be connected to a control system that controls the movement of the sample positioner.

In some embodiments, in additional to the components described above, an article may optionally comprise one or more of an outer chamber, a temperature controller, a mixer, a buffer circulators, fluid inlet, or fluid outlet. In some embodiments, the article may comprise an outer chamber that surrounds at least a portion of the chamber 125. The outer chamber may contain a fluid. In some instances, the outer chamber is connected to a fluid recirculation system configured to transport fluid into and out of the chamber via one or more fluid inlet and outlet. In some embodiments, the outer chamber and the chamber may be in fluid communication with one another via the semipermeable material. In some embodiments, the article comprises one or more buffer circulator in fluid communication with the outer chamber and/or chamber. The buffer circulator may be used to replace, replenish, or move buffer within at least a portion of a chamber (e.g., outer chamber). In some embodiments, the article may comprise a temperature controller. The temperature controller may be used to control the temperature of the fluid in at least a portion of the article. For instance the temperature controller may be used to control the temperature of at least a portion of the fluid in the outer chamber and/or the chamber. In some embodiments, the article may comprise a mixer that allows for the mixing of one or more fluid prior to entering a chamber and/or the mixing of one or more fluid in one or more chamber.

In some embodiments, a molecule, as described herein, may be or comprise a macromolecule (e.g., polymer), a biological macromolecule, a ligand, polynucleotide, oligonucleotide, protein, antibody, small molecule (e.g., organic, inorganic), nucleic acid, polysaccharides, or biologic. In certain embodiments, more than one type of molecule may be moved into, within, or from a matrix. In some such cases, the molecules may be of the same type or different type and may be selected from the above-referenced group. In some embodiments, the molecule may be a photoluminescent molecule or comprise a photoluminescent molecule, such as a dye, a fluorescent molecule, or another photoluminescent molecule. In embodiments in which the molecule is or comprises a dye, the dye may be used for in vitro imaging. In some embodiments, the molecule may be or comprise a pharmaceutically active agent (i.e., a drug). A pharmaceutically active agent may be any bioactive agent. In some embodiments, the pharmaceutically active agent may be selected from "Approved Drug Products with Therapeutic Equivalence and Evaluations," published by the United States Food and Drug Administration (F.D.A.) (the "Orange Book"). In embodiments in which the molecule is or comprises a pharmaceutically active agent (i.e., a drug), the pharmaceutically active agent may be driven into a matrix and the matrix comprising the pharmaceutically active agent may be used for therapeutic applications.

In some embodiments, a matrix, as described herein, may be or comprise a biological system (e.g., tissue, cell), polymer matrix (e.g., cross-linked, uncross-linked), biologically derived matrix, inorganic matrix, organic matrix, or combinations thereof. In some embodiments, the matrix may be a biological matrix. As used herein, a biological matrix may refer to a matrix comprising at least one biological cell. The cell may be living or non-living cell (e.g., prokaryotic cell, eukaryotic cell). Non-limiting examples of biological matrices include a single cells, single cell organisms (bacteria), multi-cellular organisms, cell aggregates, biological tissues, or whole organs, or combinations thereof. In some embodiments, the biological matrix may comprise one or more biological tissue (e.g., nervous tissue). Non-limiting examples of suitable tissues include connective tissue, nervous tissue, muscle tissue (e.g., skeletal muscle tissue, cardiac muscle tissue, smooth muscle tissue), and epithelial tissue. In some embodiments, the biological matrix may be a whole organ (e.g., brain) or a portion of an organ. Non-limiting examples of organs that can be used, in part or whole, as a biological matrix include brain, heart, lung, intestine, stomach, spleen, skin, liver, prostate, bladder, pancreas, thyroid, kidney, bone, spinal cord, and eye, amongst others. In some embodiments, the matrix may be a polymer matrix. Any suitable polymer matrix may be used.

In some instances, the polymer matrix may be charged polymer matrix. In certain embodiments, the matrix may be a gel (e.g., hydrogel).

As described herein, a matrix may be a biological matrix. In some such embodiments, the cell may be a bacterium or other single-cell organism, a plant cell, fungal cell, or an animal cell. In some embodiments, the cell may be a single-cell organism. Non-limiting examples of single-cell organisms include a protozoan, a trypanosome, an amoeba, a yeast cell, and algae. In certain embodiments, the cell may be an animal cell. Non-limiting examples of the animal cells include, an invertebrate cell (e.g., a cell from a fruit fly), a fish cell (e.g., a zebrafish cell), an amphibian cell (e.g., a frog cell), a reptile cell, a bird cell, and a mammalian cell (e.g., human cell, primate cell, a bovine cell, a horse cell, a porcine cell, a goat cell, a dog cell, a cat cell, a cell from a rodent such as a rat or a mouse). In some embodiments, the cell can be a human cell. In some embodiments, the cell may be from a multi-cellular organism. For example, the cell may be a neural cell, a cardiac cell, a fibroblast, a keratinocyte, a hepatocyte, a chondrocyte, a osteocyte, a muscle cell, a blood cell, an endothelial cell, an immune cell (e.g., a T-cell, a B-cell, a macrophage, a neutrophil, a basophil, a mast cell, an eosinophil), or a stem cell.

In some embodiments, a molecule and a binding partner may associate via a chemical and/or biological interaction. In some embodiments, a molecule and a binding partner may associate via a chemical interaction, such as a chemical bond. The chemical bond may be a covalent bond or non-covalent bond. In some cases, the chemical bond is a non-covalent bond such as a hydrogen bond, ionic bond, dative bond, and/or a Van der Waals interaction. In some embodiments, the molecule and binding partner may comprise functional groups capable of forming such bonds. For example, a molecule may include at least one hydrogen atom capable of interacting with a pair of electrons on a hydrogen-bond acceptor of a binding partner to form the hydrogen bond. In some embodiments, a molecule and/or a binding partner may include an electron-rich or electron-poor moiety, such that it may form an electrostatic interaction with another of a binding partner and/or molecule, respectively. It should be understood that covalent and non-covalent bonds between components may be formed by any type of reactions, as known to those of ordinary skill in the art, using the appropriate functional groups to undergo such reactions. Chemical interactions suitable for use with various embodiments described herein can be selected readily by those of ordinary skill in the art, based upon the description herein.

In some embodiments, an association between a molecule and a binding partner may occur via a biological binding event (i.e., between complementary pairs of biological molecules). For example, a molecule may include an entity such as biotin that specifically binds to a complementary entity, such as avidin or streptavidin, on the binding partner. Other examples of biological molecules that may form biological bonds between pairs of biological molecules include, but are not limited to, proteins, nucleic acids, glycoproteins, carbohydrates, hormones, and the like. Specific examples include, but are not limited to, an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Biological interactions between a molecule and a binding partner suitable for use in the embodiments described herein can be selected readily, by those of ordinary skill in the art, based upon the description herein as their function, examples of such biological interactions, and knowledge herein and in the art as to simple techniques for identifying suitable chemical interactions.

In some embodiments, the condition that inhibits, facilitates, or enhances the association between a molecule and a binding partner may be one of pH, ionic concentration, concentration of a chemical species (e.g., formaldehyde, surfactant), or temperature. Those of ordinary skill in the art would be aware of conditions that can inhibit, facilitate, or enhance the association between a molecule and a binding partner.

As described herein, a molecule and/or matrix may be charged. In general, the molecule to be moved by the electric field is charged or a precursor to a charged molecule. In some embodiments, the methods and articles, described herein, may be particularly well suited for the movement of charged molecules in the presence of a charged matrix. As used herein, the term "charged molecule" and "charged matrix" have their ordinary meaning in the art and may refer to a molecule or matrix comprising one or more charged moiety. As used herein, a "charged moiety" is a chemical moiety that carries a formal electronic charge, e.g., monovalent (+1), divalent (+2), trivalent (+3), etc. The charged moiety may be anionic (i.e., negatively charged) or cationic (i.e., positively charged). Examples of negatively-charged groups or precursors thereof, include carboxylate groups, sulfonate group, sulfate groups, phosphonate groups, phosphate groups, hydroxyl groups, and the like. Examples of positively-charged moieties include amine groups (e.g., primary, secondary, and/or tertiary amines), ammonium groups, pyridinium group, and imidizolium groups. In a particular embodiment, the charged moieties comprise sulfonate groups. In some embodiments, the charged moiety may comprise —OH, —NH$_3$+, —COO—, —SH, —CHO, a ketone, an azide, and/or a halide. The charge of the charged moiety may vary, in some cases, with the environmental conditions, for example, changes in pH may alter the charge of the moiety, and/or cause the moiety to become charged or uncharged. Typically, the charge of a moiety is determined under environmental conditions at which the molecule and/or matrix is used. In general, the charge density of the molecule and/or matrix may be selected as desired.

In some cases, the molecule and/or matrix may include one or more precursor moieties that can be converted to charged moieties. For instance, the molecule and/or matrix may include a neutral moiety that can be hydrolyzed to form a charged moiety, such as those described above. As non-limiting specific examples, the matrix may include t-butyl acrylate and/or t-butyl methacrylate, which can be hydrolyzed to form an acrylic acid or a methacrylic acid, respectively. Those of ordinary skill in the art will be able to determine whether a given chemical moiety carries a formal electronic charge (for example, by inspection, pH titration, ionic conductivity measurements, etc.), and/or whether a given chemical moiety can be reacted (e.g., hydrolyzed) to form a chemical moiety that carries a formal electronic charge.

It should be understood the terms "charged" or "charged moiety" does not refer to a "partial negative charge" or "partial positive charge" on a molecule or matrix. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

As described herein, an electric field may be used to move molecules into, within, or from at least a portion of a matrix. In general, the magnitude of the electric field may be selected as desired for a given application. For instance, in some embodiments, magnitude of the electric field may be greater than or equal to about 1 V/m, greater than or equal to about 2 V/m, greater than or equal to about 3 V/m, greater than or equal to about 5 V/m, greater than or equal to about 10 V/m, greater than or equal to about 20 V/m, greater than or equal to about 40 V/m, greater than or equal to about 50 V/m, greater than or equal to about 75 V/m, greater than or equal to about 100 V/m, greater than or equal to about 200 V/m, greater than or equal to about 500 V/m, greater than or equal to about 1,000 V/m, greater than or equal to about 2,500 V/m, greater than or equal to about 5,000 V/m, greater than or equal to about 10,000 V/m, greater than or equal to about 25,000 V/m, greater than or equal to about 50,000 V/m, or greater than or equal to about 75,000 V/m. In some instance, the magnitude of the electric field may be less than or equal to about 100,000 V/m, less than or equal to about 75,000 V/m, less than or equal to about 50,000 V/m, less than or equal to about 25,000 V/m, less than or equal to about 10,000 V/m, less than or equal to about 5,000 V/m, less than or equal to about 2,500 V/m, less than or equal to about 1,000 V/m, less than or equal to about 500 V/m, less than or equal to about 200 V/m, less than or equal to about 100 V/m, less than or equal to about 50 V/m, or less than or equal to about 10 V/m. Combination of the above-referenced ranges are also possible (e.g., greater than or equal to about 10 V/m and less than or equal to about 100,000 V/m, greater than or equal to about 20 V/m and less than or equal to about 100,000 V/m). Other values are also possible. It should be understood that the magnitude of an electrodynamic field may refer to the average magnitude of the field or any magnitude used in the dynamic field. In some embodiments, a higher electric field magnitude may be achieved without adversely affecting the matrix using an electric dynamic field.

In some embodiments, a dynamic electric field may be used to move molecules with respect to a matrix. In certain embodiments, at least one or more property of the electric field may changes as a function of time. In some instances, the frequency of the changes in one or more property of the electric field may be greater than or equal to about 0.0001 Hz, greater than or equal to about 0.001 Hz, greater than or equal to about 0.01 Hz, greater than or equal to about 0.1, Hz greater than or equal to about 1 Hz, greater than or equal to about 5 Hz, greater than or equal to about 10 Hz, greater than or equal to about 20 Hz, greater than or equal to about 50 Hz, greater than or equal to about 100 Hz, greater than or equal to about 250 Hz, greater than or equal to about 500 Hz, greater than or equal to about 750 Hz, greater than or equal to about 1,000 Hz, greater than or equal to about 5,000 Hz, greater than or equal to about 10,000 Hz, greater than or equal to about 50,000 Hz, greater than or equal to about 100,000 Hz, or greater than or equal to about 500,000 Hz. In some instances, the frequency of the changes in one or more property of the electric field may be less than or equal to about 1,000,000 Hz, less than or equal to about 500,000 Hz, less than or equal to about 100,000 Hz, less than or equal to about 50,000 Hz, less than or equal to about 10,000 Hz, less than or equal to about 5,000 Hz, less than or equal to about 1,000 Hz, less than or equal to about 750 Hz, less than or equal to about 500 Hz, less than or equal to about 250 Hz, less than or equal to about 100 Hz, less than or equal to about 50 Hz, less than or equal to about 20 Hz, less than or equal to about 10 Hz, less than or equal to about 5 Hz, or less than or equal to about 1 Hz. Combination of the above-referenced ranges are also possible (e.g., greater than or equal to about 0.0001 Hz and less than or equal to about 10,000 Hz, greater than or equal to about 0.0001 Hz and less than or equal to about 100 Hz). Other values are also possible.

In some embodiments, two or more properties of the electric field may change as a function of time. In some such embodiments, two or more of the properties may change at the same or different frequencies. In some embodiments, two or more of the properties may change at the same frequency. For example, the magnitude and direction of the electric field may change at the same or different frequencies. In some embodiments, one or more property may have a first frequency over a first time frame and a second frequency over a second timeframe. For example, the direction of the electric field may have a frequency of 0.01 Hz for 5 minutes and a frequency of 10 Hz for 3 minutes. In some embodiments, a property that has a certain frequency may change at regular, irregular, and/or stochastic intervals. For instance, an electric field may have a frequency of 1 Hz but the direction of an electric field may change such that the electric field has a first direction for 0.75 seconds and a second direction for 0.25 seconds. In other instances, an electric field may also have a frequency of 1 Hz but the direction of an electric field may change such that the electric field has a first direction for 0.5 seconds and a second direction for 0.5 seconds.

In general, an electric field may be generated using any method known to those of ordinary skill in the art. In some embodiments, the electric field may be a one-dimensional, two-dimensional, or three-dimensional electric field. In some embodiments, a multi-dimensional electrodynamic field may be dynamic in one or more dimensions.

In general, a chamber (e.g., chamber, outer chamber) may have any suitable shape or dimension. In some embodiments, the dimensions of the chambers may be selected as desired. It should be understood that a chamber can have any suitable cross-sectional dimension. For instance, in some embodiments, chamber may have a maximum cross-sectional dimension of greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, a chamber, may have a maximum cross-sectional dimension of less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values of maximum cross-sectional dimensions are also possible.

In some cases, at least one or at least two cross-sectional dimensions (e.g., a height and a width) of chamber may be greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, at least one or at least two cross-sectional dimensions of chamber may be less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values are also possible.

A chamber may have a certain width-to-height ratio. In certain instances, the ratio of the width to height of chamber may be greater than or equal to about 1:1, greater than or equal to about 2:1, greater than or equal to about 5:1, greater than or equal to about 10:1, greater than or equal to about 15:1, or greater than or equal to about 20:1. In some instances the width-to-height ratio may be less than or equal to about 30:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

As described herein, at least a portion of the chamber may be defined by a semipermeable material. In some embodiments, the semipermeable material may form a portion of one or more wall of the chamber. In certain embodiments, the percentage of one or more wall of the chamber or the entire chamber that is defined by a semipermeable material may be greater than or equal to about 1%, greater than or equal to about 5%, greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, greater than or equal to about 90%, greater than or equal to about 95%, or greater than or equal to about 97%. In some embodiments, the percentage of one or more wall of the chamber or the entire chamber that is defined by a semipermeable material may be less than or equal to about 100%, less than or equal to about 95%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., greater than or equal to about 5% and less than or equal to about 90%, greater than or equal to about 5% and less than or equal to about 100%). Other values are also possible.

In general, the sample positioner may have any suitable shape or dimension. In some embodiments, the sample positioner may occupy a significant portion of the chamber. For instance, in some embodiments, the ratio of the cross-sectional area of the chamber to the cross-sectional area of the sample positioner may be less than or equal to about 30:1, less than or equal to about 20:1, less than or equal to about 15:1, less than or equal to about 10:1, less than or equal to about 5:1, or less than or equal to about 2:1. In some instances the ratio of the cross-sectional area of the chamber to the cross-sectional area of the sample positioner may be greater than or equal to about 1:1, greater than or equal to about 1.5:1, greater than or equal to about 2:1, greater than or equal to about 5:1, greater than or equal to about 10:1, greater than or equal to about 15:1, or greater than or equal to about 20:1. Combinations of the above-referenced ranges are also possible (e.g., greater than or equal to about 1:1 and less than or equal to about 20:1). Other values are also possible.

In some embodiments, the dimensions of the sample positioner may be selected as desired. It should be understood that a sample positioner can have any suitable cross-sectional dimension. For instance, in some embodiments, sample positioner may have a maximum cross-sectional dimension of greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, a sample positioner, may have a maximum cross-sectional dimension of less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values of maximum cross-sectional dimensions are also possible.

In some cases, at least one or at least two cross-sectional dimensions (e.g., a height and a width) of sample positioner may be greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, at least one or at least two cross-sectional dimensions of sample positioner may be less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values are also possible.

A sample positioner may have a certain width-to-height ratio. In certain instances, the ratio of the width to height of chamber may be greater than or equal to about 1:1, greater than or equal to about 2:1, greater than or equal to about 5:1, greater than or equal to about 10:1, greater than or equal to about 15:1, or greater than or equal to about 20:1. In some instances the width-to-height ratio may be less than or equal to about 30:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

The term antibody refers to an immunoglobulin or parts thereof, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

A biological macromolecule is a polynucleotide (e.g., RNA, DNA, RNA/DNA hybrid), protein, peptide, lipid, natural product, or polysaccharide. The biological macromolecule may be naturally occurring or non-naturally occurring. In a preferred embodiment, a biological macromolecule has a molecular weight greater than 500 g/mol.

A ligand refers to any chemical compound, polynucleotide, peptide, protein, lipid, carbohydrate, small molecule, natural product, polymer, etc. that has a binding affinity for a target (e.g., a protein, carbohydrate, lipid, peptide, macromolecules, biological macromolecules, oligonucleotide, polynucleotide). Preferably, the target is a protein. In some embodiments, the ligand is specific for its target. In some embodiments, the ligand has a binding affinity for the target in the range of 100 mM to 1 pM, preferably 1 mM to 1 pM, more preferably 1 µM to 1 pM. The ligand may bind to its target via any means including hydrophobic interactions, hydrogen bonding, electrostatic interactions, van der Waals interactions, pi stacking, covalent bonding, magnetic interactions, etc.

Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

A protein comprises a polymer of amino acid residues linked together by peptide (amide) bonds. The term, as used herein, refers to proteins, polypeptides, and peptides of any size, structure, or function. Typically, a protein will be at least three amino acids long, preferably at least 10 amino acids in length, more preferably at least 25 amino acids in length, and most preferably at least 50 amino acids in length. Proteins may also be greater than 100 amino acids in length. A protein may refer to an individual protein or a collection of proteins. A protein may refer to a full-length protein or a fragment of a protein. Inventive proteins preferably contain only natural amino acids, although non-natural amino acids and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a myristoyl group, a fatty acid group, a linker for conjugation, functionalization, or other modification, etc. A protein may also be a single molecule or may be a multi-molecular complex comprising proteins, lipids, RNA, DNA, carbohydrates, etc. A protein may be a natural or unnatural fragment of a naturally occurring protein or peptide. A protein may be naturally occurring, recombinant, or synthetic, or any combination of these.

The term small molecule, as used herein, refers to an organic or inorganic compound either synthesized in the laboratory or found in nature which has a molecular weight of less than about 2000 g/mole, or less than about 1000 g/mole, and even less than about 500 g/mole. Small molecules, as used herein, can refer to compounds that are "natural product-like", such as small molecule that are similar in structure to a natural product or are similar with respect to density of stereocenters, density of functional groups, ring systems, 3-D structure, etc.; however, the term "small molecule" is not limited to "natural product-like" compounds and may include compounds that are not based on and are not similar to known natural products. Small molecules may include, for example, nucleic acids, peptides, polypeptides, peptide nucleic acids, peptidomimetics, carbohydrates, lipids or other organic (carbon containing) or inorganic moieties.

The following examples are intended to illustrate certain embodiments of the present invention, but do not exemplify the full scope of the invention.

Example 1

This example describes the use of an electric field to transport molecules into a matrix.

Comprehensive understanding of biological systems has been hindered by the absence of tools that enable optical and molecular interrogation of unsectioned, thick tissues in a practical timeframe. This example demonstrates a novel technique based on electrophoretic movement to address this problem. The technique was applied to the whole mouse brain tissue and the whole mouse brain tissue could be stained in a couple of days.

A significant challenge across fields of biological sciences, and especially neuroscience, has been to extract detailed structural and molecular information from complex biological systems. Most investigations of a biological system, such as fixed brain tissue, heavily relies on labeling the structures or molecules of interest followed by microscopy. Labeling techniques such as immunohistochemistry and in situ hybridization are in routine practice in most labs in biomedicine, and technological innovations in optical microscopy have enabled observation of tiny details of tissue structure at subcellular resolution. However, most often the process requires sectioning of thick tissue into μm- or nm-thin slices for both photons and visualizing molecular probes to thoroughly penetrate the depth, which are time-consuming, error-prone and either laborious or expensive when automated. Optical clearing methods that increase the depth of light microscopy have been developed to image thick tissues without sectioning, but these methods do not enhance macromolecule penetration and therefore are not compatible with molecular phenotyping throughout the entire volume. As a first step to overcome these problems, a technique that renders thick tissue optically transparent and macromolecule-permeable has been developed. This technique enables complete access to whole mouse brain and thick postmortem human brain tissue via both light microscopy and molecular phenotyping techniques such as immunohistochemistry and in situ hybridization. However, molecular interrogation (e.g., staining) in these transparent tissues is still impractically slow, because passive diffusion of probe molecules (e.g. antibodies) throughout the entire tissue thickness, in case of a whole adult mouse brain, takes many weeks to months.

To address these limitations, an electric field was used to move charged molecules through the dense tissue many orders of magnitude faster than diffusion, with velocity proportional to the quadratic of the strength of the electric field. Therefore, electrophoretic movement was used to rapidly and actively transport charged molecules with desired functionality—such as detergent molecules for lipid removal or antibody molecules for immunolabeling—through the thick tissue, allowing for fast optical clearing and molecular phenotyping. Furthermore, by strategically optimizing macrofluidic circuit arrangement and adjusting the composition, temperature, and viscosity of the solution, one can concentrate the current flow to the tissue and expedite the process.

In the presence of a concentration gradient, the action of molecular diffusion (i.e. Brownian motion) in reducing that concentration gradient results in net mass transport down the concentration gradient. This is why when a tissue free of a particular antibody is placed in a bath containing that antibody, antibodies diffuse into the tissue, albeit slowly. This passive diffusion is orders of magnitude slower than electromigration, where charged molecules move down an electric potential gradient (FIG. 8). But this powerfully directed motion causes stress on the tissue and sometimes irretrievably deforms the tissue. If, however, the electric field rotates with respect to the tissue, net stress can be minimized while the mass transport into the tissue enhanced via electrophoretic dispersion. Theory predicts that effective diffusivity is approximately quadratic with respect to the magnitude of the velocity resulting from electromigration and thus improves the transport of charged molecules. In this experimental set-up consisting of 50 V and 0.5 rpm, the diffusivity of the antibody increased four orders of magnitude in accordance with the theory.

To make the whole mouse brain transparent, acrylamide monomers, formaldehyde and polymerization initiators were infused into the brain at 4° C. to crosslink the tissue and to link acrylamide molecules to the tissue. Thermally triggering polymerization reaction at 37° C. formed a tissue-acrylamide polymer hybrid construct. Then the tissue-polymer hybrid was subject to electrophoresis in ionic detergent solution for the removal of lipids and other un-crosslinked molecules. To expedite the clearing process (and also for subsequent rapid molecular labeling), we designed a new electrophoresis device that involved a large amount of outer channel circulation and a small amount of inner circulation (FIG. 8B-E). An important feature of this device was the spatial isolation of central tissue-containing reaction chamber (a part of inner circulation) from surrounding electrolysis chamber (a part of outer circulation) by nanoporous semi-permeable membranes (FIG. 8). This allowed independent and versatile control of solution composition, temperature, conductivity and reaction volume in reaction and electrolysis chambers to be achieved.

Firstly, isolation of center chamber allowed for the use of dramatically reduced amount of reactants, such as detergent or antibody molecules that are costly, while keeping high concentration, as large volume of buffer solutions circulated the electrolysis chamber and outer channels. Second, this configuration prevented the reactants from directly contacting the electrodes, thereby preventing consumption of reactant molecules by electrochemical reaction and generation of harmful by-products that may damage the tissue. Third, buffer with high salt concentration for could be used for the electrolysis chamber and low salt-containing buffer for the reaction chamber, thereby increasing the resistance of the reaction chamber and voltage drop between the ends of reaction chamber. Finally, the temperature of the solution (and therefore viscosity) could selectively be decreased in the reaction chamber to further increase the resistance of the solution. By optimizing salt concentration and temperature, the voltage drop was able to be increased between the ends of reaction chamber nearly tenfold after optimization (data not shown). Cooling was important because fluorophores already being expressed in the tissue may become quenched above 37° C. Without circulation of solutions the temperature can easily go beyond 37° C. Cooling and circulation made it possible to apply high voltage.

The tissue-polymer hybrid was placed on the holder that was attached to a step motor for rotation. Rotation allowed the uniform distribution of charged molecules throughout the specimen and to prevent tissue deformation during the clearing procedure. Another key feature was macrofluidic arrangements. Incoming solution effectively washed out the products of electrolysis, preventing concentration of acids or bases at each electrode. The charge of the protein was controlled by changing the pH. At high pH, most proteins had net negative charges.

FIG. 8 illustrates the principles and implementation of electrophoretic random walk. FIGS. 8A-8C show the comparison of Brownian random walk (top) with electrophoretic linear transport (middle) and electrophoretic random walk (bottom). Computer simulation results (A), schematic diagram (B) and immunostaining results (C) are shown. Circles 1 and 2 represent charged particles of the same mass, and black dot represent a particle with smaller mass. Particle 2 bears higher charge than particle 1. In Brownian random walk, particles make small random movements, resulting in a small net displacement. Therefore, tissue penetration of the particles is slow and molecules accumulate in the surface. In the electric field, particles with higher charge moves faster than particles with smaller charge. Charged molecules can rapidly penetrate through the tissue, but their distribution follows electric field gradient. Also this causes stress on the tissue and sometimes can irretrievably deform the tissue. Rotating the tissue in the electric field mimics Brownian random walk but with large net displacement of particles. Uniform distribution of particles can be achieved by electrophoretic random walk. Results shown in FIG. 8C were obtained by immunostaining of eGFP in Thy1-eGFP mice. Note signals from the Alexa 555-conjugated eGFP antibody are uniformly distributed across the brain. FIG. 8D is an image of the device. Electrophoresis chamber consists of an inner chamber and two outer chambers. Inner chamber has a lid with a step motor and its controller. FIG. 8E is a bird's eye view of the device. The inner chamber was separated from outer chambers by nanoporous membranes and tissue was able to rotate inside. The outer chambers on each side contained platinum wires for electrophoresis. FIG. 8F is a top view of the device. The tissue sample was isolated from the electrochemical reactions in both electrodes. As nanoporous membranes were not permeable to large molecules, such molecules with desired properties were confined to the small volume of the inner chamber and were uniformly distributed.

FIG. 9 illustrates the electrophoretic random walk with dynamic affinity shift that allowed for the rapid and uniform immunolabeling of large intact tissues. FIG. 9A is a schematic of the immunolabeling device. For this experiment, 13 ml of lithium borate buffer (50 mM, pH 11) containing antibodies was loaded in the inner chamber and a large volume of cooled lithium borate buffer (50 mM; pH 9; 4° C.) was circulated through the outer chambers. 50V was applied across the inner chamber. The small buffer molecules could freely pass through the nanoporous membrane, but antibodies were secured within the inner chamber. This unique design protected the important biomolecules from degradation by electro-oxidation/reduction. FIG. 9B illustrates the time-course of pH change in the inner chamber during the electrophoresis. Free movement of buffer ions across the nanoporous membrane naturally decreased the pH of the buffer from 11 to 9 over ~4 hours. n=4. FIG. 9C is a representative images of 1-mm thick Thy1-eGFP brain sections stained against eGFP at buffers with different pH. Higher antibody-antigen binding occurred at pH 9. FIG. 9D is a schematic of antibody penetration and distribution throughout the tissue over time. Antibody molecules are highly charged at high pH; therefore, tissue penetration and uniform distribution of antibodies under the electrophoretic random walk regime was the most efficient at high pH. As pH decreased, distributed antibodies start to bind their target antigens. FIG. 9E are representative images of whole Thy1-eGFP mouse brains stained against eGFP (left) only with electrophoresis, (middle) with electrophoresis and rotation and (right) with electrophoresis, rotation and dynamic affinity shift.

FIG. 10 illustrates the rapid clearing and immuno staining of thick human brain samples. FIG. 10A is a schematic of the clearing setup. Charged SDS micelles were confined in the inner chamber by nanoporous membranes and were actively transported through the rotating tissue, mimicking random walk. SDS micelles were not able to cross the nanoporous membranes, whereas SDS monomers were. FIG. 10B is a graph of the pH change over time for the present technique (new clarity) and a previous technique (old clarity) that shows that the present technique does not cause drop in pH. FIG. 10C are representative images of cleared brains at different time points. The present technique more rapidly clears the brain than old CLARITY. FIG. 10D shows the uniform and complete immunostaining of thick human brain tissue was possible with the present technique. FIG. 10E-G show high-magnification images of brain tissue. FIG. 10H shows a graph of the dendritic bridges/neurons for a given large of the brain as determined using the present technique.

Example 2

This example describes a transport method, referred to in this example as stochastic electrotransport, which allows rapid and selective transport of charged molecules without disrupting the surrounding charged matrix. Initially, a device was designed to implement stochastic electrotransport of detergent micelles to enable rapid and uniform clearing of intact tissues. With this device, a whole adult mouse brain tissue was cleared in as short as 3 days. Next, a modified device was designed to implement stochastic electrotransport of molecular probes to allow for the rapid and uniform staining of intact tissues. The versatility of this approach was demonstrated by staining a cleared hydrogel whole adult mouse brain with synthetic nuclear stains, carbohydrate-binding proteins, and antibodies. The technique resulted in strikingly uniform and rapid labeling of various biomolecules in organ-scale mammalian tissues. Taken together, stochastic electrotransport further facilitated rapid and multi-dimensional interrogation of large-scale intact biological systems.

A sufficiently strong electric field can expedite the transport of ions with their velocity linearly dependent on their electromobility, while non-charged materials (e.g. polyacrylamide and agarose gels) remain stationary. Stationary electric gradient, however, can irreversibly deform the surrounding matrix if the matrix itself is charged. Charged ionic matrices are commonly found and include all biological tissues, but one specific example is a cleared hydrogel-tissue hybrid. In certain hydrogel-tissue hybrids, the small building blocks of the hydrogel mesh are infused into a tissue and subsequently polymerized to form an interconnected nanoporous mesh. During this process, endogenous biomolecules (e.g. nucleic acids, proteins, and small molecules) are preserved at their physiological location by crosslinking to the synthetic polymer chains and certain molecules (e.g., lipids) are removed from the tissue to produce an optical transparent ("cleared") hydrogel-tissue hybrid. Although the high degree of crosslinking necessary to preserve the physiological architecture significantly lowers the electromobility of the crosslinked molecules, these crosslinked molecules slowly migrate under a directed electric field and may damage the matrix.

To address this problem, stochastic electrotransport, which selectively expedites the transport of freely moving charged molecules without damaging the surrounding charged matrix, was developed as described in this example. Stochastic electrotransport hinges on the idea that a stochastic electric field can selectively enhance the transport of particles with large electromobilities by inducing an electrically-driven 'random walk'. Our computational simulation using a Kinetic Monte Carlo model predicted that in the presence of a locally stochastic electric field caused by a dynamically changing electric field and a chaotic distribution of pores, the mean squared displacement, $<R^2>$, of particles scales quadratically with the product of their electromobilities and the field strength (normalized by effective rotation time scale P and experiment time t).

This unique quadratic dependence allowed the selective increase in the transport of only highly electromobile particles (e.g. antibodies) to several orders of magnitude greater than passive diffusion while suppressing the movement of tethered molecules (e.g. endogenous antigens) with low electromobility. For instance, in stochastic electrotransport of molecular probes within tissues, a condition that induces 1-mm displacement of probes would move crosslinked endogenous biomolecules by only 1-nm (vs 1-µm in static electrophoresis) assuming that the electromobility of the former is three orders of magnitude higher than that of the latter. Therefore, the charged matrix could remain virtually stationary while unbound functional molecules rapidly disperse throughout the matrix.

First, this new transport strategy was applied to transporting detergent sodium dodecyl sulfate (SDS) micelles for expediting extraction of lipids from hydrogel-embedded intact tissues. With certain static electrophoresis techniques, fully clearing a whole adult mouse brain takes several weeks. Applying higher voltage across the tissue would expedite the process, but this would come at the cost of tissue deformation due to the static electrophoresis. Furthermore, increasing voltage causes overheating of the tissue, facilitates undesired consumption of detergent by electrodes, and expedites accumulation of by-products of electrolysis that can adversely affect the tissue sample (e.g. pH of the circulating solution drops rapidly and can denature the proteins).

Figure 11A:
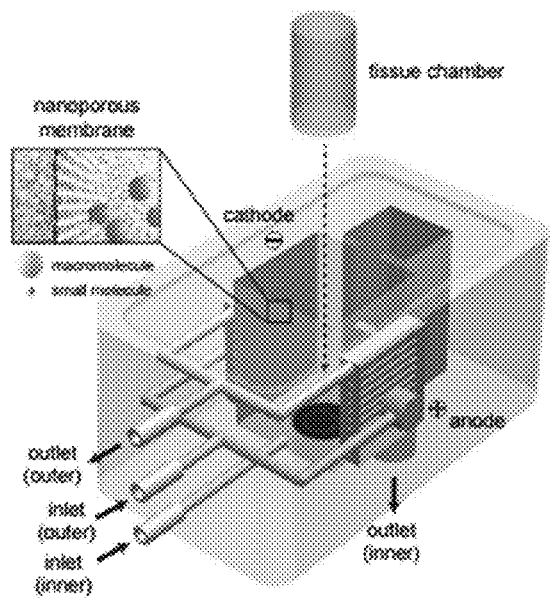
FIG. 11A illustrates an article for the electrophoretic movement of molecules, according to certain embodiments.

To address these problems and effectively implement stochastic electrotransport of SDS micelles, a novel integrated platform with several key features was built. The device is shown in FIG. 11A. First, a sample was continuously rotated with respect to an electrostatic field to create an electric force that dynamically changed with time in both direction and magnitude. This electrodynamic field, combined with the chaotically distributed pores within the tissue sample, generated an electrophoretically driven random walk of charged molecules. Second, nanoporous membranes was introduced to separate "inner" and "outer" channels that circulated clearing buffer (200 mM SDS, 10 mM lithium borate, pH 9) and electrophoresis buffer (10 mM SDS, 10 mM lithium borate, pH 9). The nanoporous membrane allowed only small chemicals including current-carrying ions and SDS monomers to move freely across the two channels, while confining large SDS micelles inside. The unique design not only kept the concentration of SDS high inside the inner channels, but also protected the sample from destructive chemical reactions and their by-products (e.g. various acids and bases.) The nanoporous membrane effectively blocked by-products of electrolysis from entering the inner circulation and thus protected the sample. An SDS concentration of 200 mM for the clearing solution was chosen because SDS micelles exhibited the highest stability and detergency at 200 mM, and 10 mM for the electrophoresis buffer so that 10 mM of SDS monomers could equilibrate across two channels, given that critical micelle concentration of SDS is ~8.3 mM. Finally, separating the circulation of inner (clearing) and outer (electrophoresis) solutions allowed the independent control of their temperatures and pH.

Figure 11B:
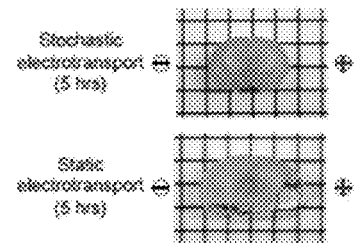
FIG. 11B illustrates a brain cleared using static electrotransport and a brain cleared by stochastic electrotransport after five hours, according to certain embodiments.
Figure 11C:
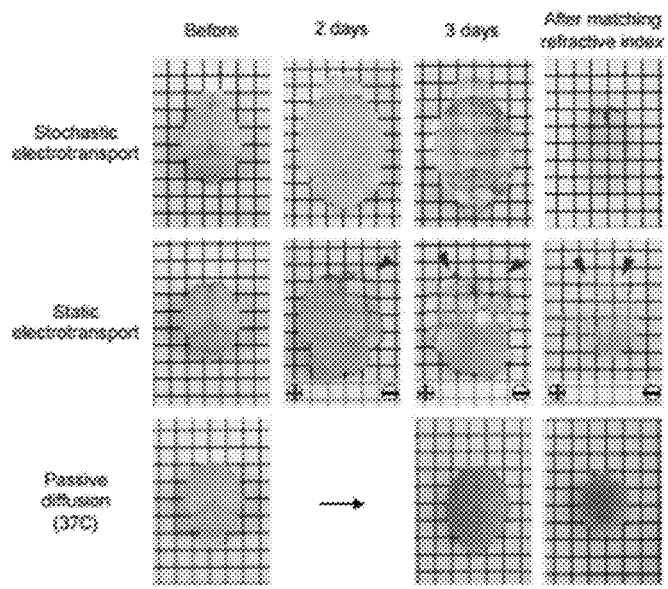
FIG. 11C illustrates a brain cleared using static electrotransport, a brain cleared using stochastic electrotransport, and a brain cleared using passive diffusion, according to certain embodiments.

To test the anticipated features of stochastic electrotransport, a hydrogel-embedded adult mouse brain tissue was placed in the device and applied either static electrotransport with tissue rotation ("stochastic electrotransport") or static electrotransport without tissue rotation ("static electrotransport") for 5 hours. As expected, notable deformation was observed in the sample subjected to static electrophoresis as shown in FIG. 11B. With stochastic electrotransport of SDS micelles, a mouse brain was completely cleared in 3 days without noticeable tissue deformation as shown in FIG. 11C (note that expansion of the tissue was reversed after incubation in the refractive index matching solution). Static electrophoresis of the tissue for the same duration severely damaged the tissue, while passive diffusion of SDS micelles could only partially clear the surface of the tissue. Taken together, these results demonstrated that stochastic electrotransport allowed the rapid clearing of intact tissue without causing deformation.

Next, the device was revised to implement stochastic electrotransport of molecular probes into the cleared tissues. Sample rotation was maintained, but the nanoporous membranes that separated inner and outer channels were removed. Instead, the sample chamber was walled with a nanoporous membrane to maintain the concentration of probes high inside the chamber and to protect the sample and probes from electrolysis and its by-products. To test the integrated system, a disk-shape acrylamide gel larger than a mouse brain (radius, 9 mm; height, 8 mm) was placed into the chamber loaded with fluorescein-conjugated bovine serum albumin (BSA-FITC) and a stochastic electric field was applied. As expected, significant enhanced diffusion-like transport of BSA-FITC into the gel and uniform dispersion of BSA-FITC was observed within three hours. Next, to test if a charged-matrix remained intact under stochastic electric field, a cleared intact mouse brain was exposed to stochastic electric field and another cleared intact mouse brain was exposed to a static electric field. Within an hour, the brain exposed to the stationary electric field was noticeably damaged, whereas the brain under the stochastic electric field remained unchanged.

Figure 12A:
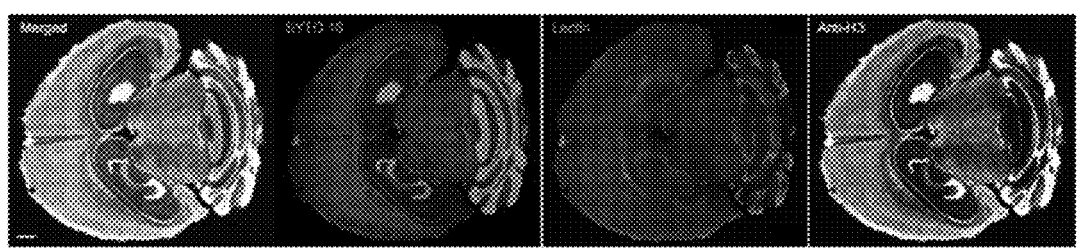
FIG. 12A illustrates a brain that was subject to electrophoretic movement of SYTO 16, Dylight 594-conjugated tomato lectin, and Alexa 647-conjugated anti-histone H3 antibodies, according to one set of embodiments.
Figure 12B:
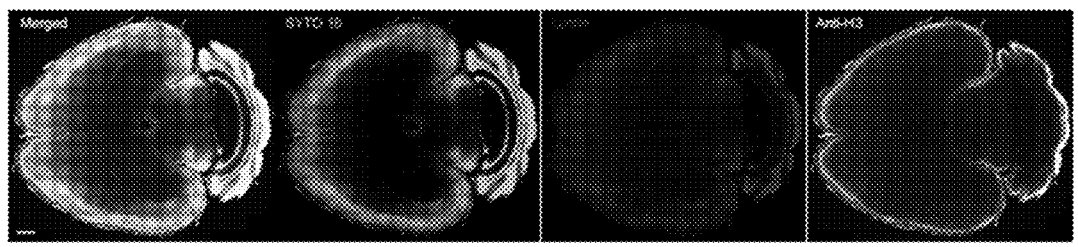
FIG. 12B illustrates a brain that was subject to passive movement of SYTO 16, Dylight 594-conjugated tomato lectin, and Alexa 647-conjugated anti-histone H3 antibodies, according to one set of embodiments.

Using this stochastic electrotransport device, several different classes of molecular probes were delivered into a cleared hydrogel whole adult mouse brain. Probes whose targets are present throughout the entire brain were chosen to thoroughly evaluate the extent to which stochastic electrotransport could achieve uniform and complete staining. SYTO 16, a widely used organic nuclear dye, fluorophore-conjugated *Lycopersicon Esculentum* (tomato) lectin, a carbohydrate-binding protein widely used as an effective blood vessel marker, and anti-histone H3 protein, an antibody against histone-H3 protein that is present in all cell nuclei were selected. Simultaneous stochastic electrotransport of these probes into a mouse brain for a day achieved remarkably uniform and complete staining of their targets in the whole brain as shown in FIG. 12A. Passive incubation of another cleared brain in the probe solution for the same duration with shaking stained only the surface with virtually no labeling at the core as shown in FIG. 12B. Among the three molecular probes, antibodies have the highest molecular weight (~150 kDa) and thus exhibited poorest penetration (~300 um) in the passive staining experiment, whereas penetration was complete throughout the entire depth of imaging in case of stochastic electrotransport. These data demonstrated that stochastic electrotransport could be used to make traditional histochemical techniques scalable to intact tissues.

Then, it was determined whether high-resolution imaging of the stochastic electrotransport-stained tissue allowed for quantitative analysis of the tissue structure. Another mouse hemisphere was subject to stochastic electrotransport of tomato lectin for 10 hours. Light-sheet microscopy was used to rapidly acquire high-resolution volume images. The acquired images displayed uniform staining of capillaries as well as larger blood vessels at different depths. A separate z-stack of images with 2 um steps was obtained within 30 seconds. Acquired images could be easily vectorized due to their high contrast and analyzed for various parameters (such as diameter, total length, and number of branch points). Such quantitative analysis of brain-wide vasculature may reveal important structural or pathological features of the vascular network in normal or diseased tissues. Thus stochastic electrotransport can be used for the rapid and quantitative phenotyping of organ-scale biological systems.

FIG. 11A shows a schematic of the device designed for implementing stochastic electrotransport for tissue-clearing. Inner circulation of the clearing solution (200 mM SDS, 10 mM LB, pH 9) and outer circulation of the electrophoresis buffer (10 mM SDS, 10 mM LB, pH 9) were separated by the nanoporous membrane (inset), which kept SDS micelles within the inner circulation and by-products of electrolytic reactions within the outer circulation. SDS monomers and buffer ions could freely move across the nanoporous membranes. SDS monomer concentration equilibrated at ~10 mM in both inner and other chambers. Voltage was applied across the inner chamber through the nanoporous membranes that passed through conductive buffer ions, and tissue chamber was placed within the inner chamber. The tissue chamber was walled with electrically resistant nylon mesh to allow for free penetration of SDS micelles and current, and rotated with respect to the electric field to produce a dynamically changing electric field. Cooled (10-20° C.) buffer solution was circulated to provide ions for electrophoresis and to remove the heat produced during electrophoresis. The pH of the inner clearing solution rapidly dropped to ~4.5 in a day without the nanoporous membrane. Stochastic electrotransport rapidly and uniformly cleared hydrogel-embedded whole adult mouse brain tissue without damaging the tissue in 3 days. Note that expansion of the tissue was reversed after incubation in the refractive index matching solution. With the same power (90 W), static electrophoresis notably deformed the tissue within as little as 5 hrs as shown in FIG. 11B and completely degraded the tissue in 3 days as shown in FIG. 11C. FIG. 11B shows coronal sections. Arrowhead points at deformed parts of the tissue. Passive diffusion of SDS at 37° C. with shaking for the same duration only partially cleared the surface. All grids are 3 mm×3 mm.

FIG. 12A shows a cleared hydrogel adult mouse brain that was subject to stochastic electrotransport of SYTO 16 (a cyanic nuclear stain), Dylight 594-conjugated tomato lectin (a carbohydrate-binding protein that labels blood vessels), and Alexa 647-conjugated anti-histone H3 antibodies (labels all cell nuclei). Horizontal sections showed uniform and complete staining of the whole brain with all three probes used. The scale bar is 1 mm. FIG. 12B shows the passive staining controls that were incubation for the same duration in 37° C. with gentle shaking. The scale bar is 1 mm.

Example 3

In this example, a new technique referred to as eTANGO (electrostochastic Transport of Activity modulated molecules in Nanoporous Gel Organ hybrid) in this example is described that allows for the virtually complete and uniform in situ molecular labeling of large-scale intact biological systems on a timescale of hours. This was achieved by integrating two new concepts: stochastic electrotransport and dynamic activity shift. Stochastic electrotransport selectively and rapidly (several orders of magnitude faster than passive diffusion) disperses only freely moving charged molecules (e.g. antibodies) without disrupting the surrounding the charged matrix (e.g. brain). Probe-target reaction kinetics are tightly controlled by dynamic activity shift to synchronize the reaction time throughout the system. The versatility of the integrated approach was demonstrate by achieving 3D visualization of cellular nuclei, vasculature, and various neuronal cell types in whole mouse using three different classes of molecular probes. The technique's specificity was also validated by staining against genetically expressed fluorescent proteins. The technique allowed strikingly uniform and rapid labeling of various biomolecules in organ-scale mammalian tissues.

To realize the potential of stochastic electrotransport, a novel integrated platform with several key features was developed. First, a sample was continuously rotated with respect to an electrostatic field to create an electric force that dynamically changed with time in both direction and magnitude. Second, the sample chamber was walled with a nanoporous membrane, allowing only small chemicals (e.g. current carrying ions, activity-modulating molecules) to move freely across the chamber while confining large probe molecules inside. This design not only kept the concentration of probes high inside the chamber, but also protected the sample and probes from destructive electrochemical reactions and their by-products (e.g. various acids and bases). Lastly, temperature-controlled buffer solution flowed around the cylindrical chamber to finely control the reaction environment (e.g. temperature and pH) within the tissue. The device was integrated the with off-device components to automate the stochastic electrotransport process.

Although stochastic electrotransport drastically shortens the time required for molecular penetration, molecular targets inside certain cleared hydrogel tissues still experienced varied reaction conditions, due to the large difference in probe migration time scale (hours) and reaction time scale (sub-seconds to minutes). If passive diffusion or stochastic electrotransport alone was applied for labeling a large-scale intact tissue, fast probe-target reaction kinetics could cause saturated labeling of the outer tissue, leaving the inner structures unexamined in some instances. To overcome this issue, binding activity of probes was dynamically modulated the during the labeling process by utilizing the fact that non-covalent binding reactions between molecules is governed by their weak interactions (e.g. electrostatic, hydrophobic, hydrogen bonding) and the strength of such forces is dependent on the surrounding chemical environment. A dynamically-adjustable environment that inhibited binding during the probe transport step and subsequently "switched-on" the reaction globally once the probes were uniformly dispersed throughout the tissue was designed. This method allows for the endogenous molecular targets in the whole tissue to experience similar reaction conditions (time and chemical concentration).

To achieve this, a universal buffer system that inhibited or significantly slowed the binding reaction for a broad range of probes from small organic molecules, carbohydrate-binding proteins, to antibodies was developed. The probes that were used are shown in Table 1. First, the ability to inhibit binding reaction by simply shifting pH from neutral to basic could was investigated. It was hypothesized that a pH shift could be used because shifting from neutral to basic pH can altered the charge of many molecules. The changing the charge of a molecule by shifting to a basic pH can disrupt or change the electrostatic interactions of the molecule that were present at a neutral pH. Using pH alone, the reaction in a subset of antibodies including α-GFP was hindered, but most probes tested showed strong reactivity in pH 11 lithium borate (LB) buffer. Next, it was determined whether adding low concentrations of ionic detergent could further decrease reactivity of probes. It is well known that detergent chemicals can disrupt molecular interactions. It was discovered that 10 mM of sodium dodecyl sulfate (SDS) could effectively inhibit or significantly slow the binding reaction in a broad range of pH and buffer systems for all probes that were tested. Using such small ionic molecules (buffer ions and SDS) as activity modulators was advantageous. The concentration of the small ionic molecules could be rapidly changed within the sample chamber by electrophoretically transporting the chemicals across the nanoporous membrane. Further, pH 11 conferred more negative charge to commonly used molecular probes (e.g. antibodies) than neutral pH, thereby enhancing electromobility. Therefore, this buffer system could be readily used with the stochastic electrotransport system, described herein, to dynamically modulate binding activity of the probes in the course of molecular labeling of intact tissues. The integration of this "'dynamic activity shift" with stochastic electrotransport is referred to in this example as eTANGO.

TABLE 1

Probes used in this Example

| Probe | Vendor | Dilution |
| --- | --- | --- |
| Alexa 647-conjugated α-eGFP antibody | Life technologies | 1:100 |
| Alexa 647-conjugated α-histone H3 antibody | Cell Signaling | (1) 1:250 (2) 1:100 |
| α-Histone H3 antibody | Abcam | 1:100 |
| α-Myelin basic protein antibody | Abcam | 1:250 |
| α-NeuN antibody | Abcam | 1:250 |
| α-Neurofilament antibody [SMI-312] | Covance | 1:250 |
| α-Parvalbumin antibody | Abcam | (1) 1:250 (2) 1:100 |
| α-Tyrosine hydroxylase antibody | Abcam | 1:150 |
| Secondary antibodies | All from Abcam | (1) 1:250 (2) 1:150 |
| PO-PRO-1 | Life Technologies | (1) 1:250 (2) 1:100 |
| DAPI | Life Technologies | 1:50,000 |
| Neurotrace 500/525 | Life Technologies | 1:250 |
| Dylight 594-conjugated tomato lectin | Vector Labs | (1) 1:250 (2) 1:50 |

To test anticipated features of the integrated eTANGO approach, nuclear staining of the whole hemisphere of an adult mouse brain with PO-PRO-1, a widely used organic nuclear dye, was performed. PO-PRO-1 exhibited strong labeling in pH 7.5 tris-borate (TB) buffer while it has nearly no signal in pH 11 LB with SDS. Also, PO-PRO-1 has two positive charges regardless of pH, making it suitable for both stochastic electrotransport and dynamic activity shift. To test if rapid and uniform nuclear staining of the intact hemisphere of a mouse brain using eTANGO could be achieved, the tissue was loaded into the sample chamber with PO-PRO-1 and a non-binding buffer (pH 11 LB buffer containing SDS), which facilitated probe transport without allowing probe-target binding reaction to occur. The same buffer with no probes was circulated through the device and a stochastic electric field was applied to drive the inactivated probes into the tissue. After five hours of stochastic electrotransport, the sample was moved to a 'binding buffer' that fostered probe-target binding reaction (pH 7.5 TB buffer) and passively incubated overnight. This approach resulted in remarkably uniform and complete nuclear staining of the whole hemisphere within only 15 hours. To assess the uniformity of the labeling achieved by the eTANGO system, middle cross-sections of the hemisphere were imaged and a simple algorithm was employed to identify nuclei based on an absolute intensity threshold and to measure the mean intensity of staining for all identified nuclei. Uniform labeling allowed such a simple algorithm to be performed precisely; if the labeling was uneven, it would have required a sophisticated algorithm to normalize different signal to noise profiles across the depth. Furthermore, the mean intensity of stained nuclei was homogeneous throughout the tissue, supporting the claim that probe targets inside the tissue experienced nearly same reaction conditions. Additional control experiments of the same duration with passive diffusion or with only stochastic electrotransport (without dynamic activity shift) caused saturated signal at the surface while virtually no labeling at the core, with stochastic electrotransport only condition yielding slightly better penetration than passive diffusion counterpart. The other control experiment with dynamic activity shift only resulted in better yet insufficient penetration of PO-PRO-1 and weak signal, because of the inherently slow nature of diffusion. These results demonstrated that eTANGO, the combination of stochastic electrotransport and dynamic activity shift, allowed for rapid, uniform, and system-wide nuclear counterstaining, which is important in histology for anatomical annotation and would be particularly useful for navigating and analyzing 3D volume datasets.

Next, it was determined if eTANGO could be used for molecular phenotyping with protein-based probes. Lectin, a carbohydrate-binding protein widely used as an effective blood vessel marker, was first tested. A fluorophore-conjugated *Lycopersicon Esculentum* (tomato) lectin showed strong binding to its targets at neutral pH but with high background in the buffers tested, whereas labeling was weaker but more specific at both neutral and basic pH in the presence of 10 mM SDS. pH 11 LB buffer with SD was used as a slow binding buffer because lectin—whose isoelectric point (pI) is 9.0—is more highly charged at basic pH, allowing faster electrophoretic transport. To minimize non-specific binding, the strong binding step was omitted. Using this simple one step approach, uniform and complete staining of the entire vasculature of a whole mouse hemisphere was achieved within 10 hours. The sample was then optically cleared using a custom-made, refractive-index-matching immersion medium. Light-sheet microscopy was used to rapidly acquire high-resolution volume images. The acquired images displayed uniform staining of capillaries as well as larger blood vessels at different depths. A separate z-stack of images with 2 um steps was obtained within 30 seconds. Acquired images could be easily vectorized due to their high contrast and analyzed for various parameters, such as diameter, total length, and number of branch points. Such quantitative analysis of brain-wide vasculature may reveal important structural or pathological features of the vascular network in normal or diseased tissues. This further extends the utility of eTANGO for rapid and quantitative phenotyping of organ-scale biological systems.

Finally, it was determined if eTANGO was compatible with immunohistochemical methods. Immunohistochemistry is one of the most commonly used molecular phenotyping techniques employing antibody-antigen binding reactions. However, due to the large size of antibodies (15 nm) and their slow mobility, antibody labeling of thick intact tissue has remained a major challenge. To investigate if eTANGO allows for rapid, complete, and uniform immunolabeling of large-scale intact tissues, eTANGO was performed to label all cellular nuclei throughout an entire mouse hemisphere using dye-conjugated α-histone H3 (H3) antibody. First, it was determined if uniform staining could be achieved using stochastic electrotransport alone. As expected and consistent with our previous experiment with PO-PRO-1, only ~200 μm-thick outer layer of the intact mouse brain was labeled with high level of background, whereas the core of the brain showed near-absence of signal, despite facilitated transport of the antibodies by stochastic electrotransport. Next, the eTANGO approach was applied. To uniformly disperse the activity-suppressed histone antibodies inside the tissue, the brain was loaded into the chamber with pH 11 LB buffer with SDS (non-binding buffer) containing dye-conjugated α-histone antibodies and an electric field was applied for 6 hours while circulating the same non-binding buffer. After this 6 hour-long non-binding step, the circulating buffer was exchanged to the binding buffer (pH 9 LB) to induce antibody-antigen binding reaction globally. pH 9 binding buffer was used instead of neutral pH to ensure that antibodies still maintained some electromobility during the binding step. In contrast to stochastic electrotransport alone control, this integrated eTANGO method resulted in complete and uniform labeling. Together, these results demonstrated that eTANGO, the integration of stochastic electrotransport and dynamic activity shift, allowed for rapid and uniform immunostaining of intact mouse brains within the timeframe of several hours.

To further validate the capabilities of eTANGO using immunohistochemical methods, α-GFP was performed staining on an intact, cleared hydrogel Thy1-eGFP adult mouse brain. The eTANGO processed brain exhibited strikingly uniform and complete α-GFP labeling of all eGFP-expressing neurons throughout the whole brain. For comparison, another brain was passively immunostained for the same duration and observed only surface-limited labeling. Detailed examination of eTANGO-stained hippocampus, cortex, and thalamus containing varying amounts of eGFP (+) neurons revealed that eTANGO was capable of uniformly immunostaining samples with heterogeneously distributed antigens. A significant amplification in signal intensity was observed in the thalamus where genetic eGFP expression was weak, which may be useful to visualize weakly expressed proteins. It was also observed that diverse brain structures at different depths could be reliably detected after eTANGO. Together, the results demonstrated that the integration of stochastic electrotransport and dynamic activity shift allowed rapid and uniform immunostaining of intact mouse brains within the timeframe of several hours.

Figure 13A:
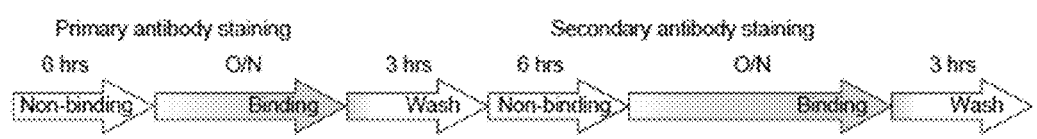
FIG. 13A illustrates a protocol for indirect immunohistochemistry, according to certain embodiments.
Figure 13B:
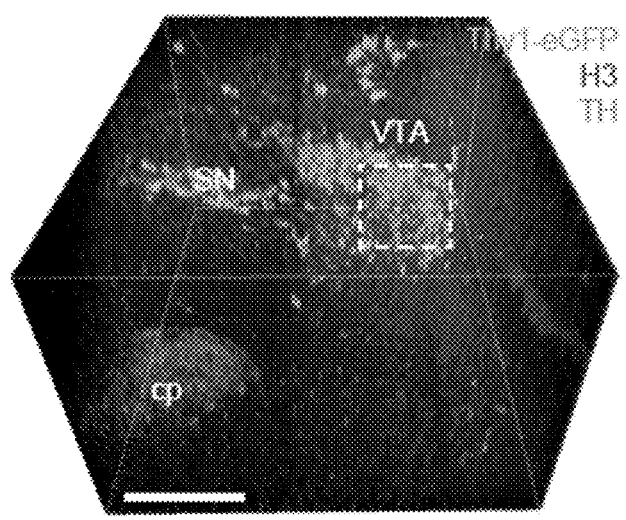
FIG. 13B illustrates a 3D rendering of the ventral tegmental area of a mouse brain after whole-brain immunostaining, according to certain embodiments.

The most widely used immunohistochemical method is indirect immunostaining—by first using target-specific primary antibody staining and then adding host-species-specific secondary antibodies that bind to the primary antibodies—as it allows signal amplification and obviates the need for conjugating fluorophores to all antigen-specific antibodies. Therefore, eTANGO was applied to indirectly immunostain various cellular markers using two consecutive non-binding and binding cycles as shown in FIG. 13A. eTANGO labeling of whole mouse brain with tyrosine hydroxylase (TH), which is an enzyme important for catecholamine biosynthesis that is commonly used for visualizing dopaminergic neurons in the midbrain areas, was performed in conjunction with H3 as a nuclear counterstain using a non-fluorophore-conjugated α-H3 antibody. As expected, α-H3 antibody labeled all nuclei, whereas strong α-TH antibody signal was restricted to well-known midbrain dopamine centers, such as the ventral tegmental area (VTA) and the substantia nigra (SN) as shown in FIG. 13B. Again, a simple intensity thresholding algorithm precisely identified H3- and TH-immunoreactive cells and counted the total number of cells and TH-expressing neurons in the medial VTA, which was possible owing to uniform labeling over the large volume.

In addition, cleared hydrogel brain tissue were stained against parvalbumin (PV)—a calcium-binding protein that has been widely used as a marker for a subpopulation of GABAergic non-pyramidal interneurons. The distribution of PV(+) neurons in the cortical layers matched previous descriptions. Surprisingly, many PV(+) neurons were found that were also eGFP(+) in ventral posterior cortical areas of Thy1-eGFP mice, which express eGFP in a subset of neurons including pyramidal neurons, indicating that some pyramidal projection neurons also express PV. It was confirmed that these neurons sent axon fibers down to the external capsule and exhibited characteristics of typical pyramidal cells, such as pyramidal soma, a large apical dendrite, a single axon, multiple basal dendrites, and dense dendritic spine. While PV-expressing projection neurons were previously described in the retrosplenial and somatosensory cortices of mice or in species other than mouse, this finding of PV(+) pyramidal neurons in other cortical areas suggest that this neural subtype may represent a distinct class of pyramidal neurons that may exist in many cortical areas. This demonstrated an example of how eTANGO allowed for the integration of multi-dimensional information—morphological, connectional, and molecular—in a non-biased manner, which may allow identification of a neural substrate underestimated by conventional approaches that examine a small region of the brain at a time.

FIGS. 13A-B show (13A) an eTANGO experimental protocol for indirect immunohistochemistry and (13B) a 3D rendering of ventral tegmental area (VTA) of a 3-month old Thy1-eGFP M line mouse brain after whole-brain immunostaining against TH and H3 with eTANGO (SN is substantia nigra and cp is cerebral peduncle) with a scale bar equal to 300 μm.

Example 4

This example describes the methods used in Examples 2 and 3.

Experimental Subjects:

Male C57BL/6 mice, aged 6-8 weeks at the start of experiments, were housed in a reverse 12-hr light/dark cycle. Food and water were given ad libitum.

Histochemistry of Sectioned Cleared Hydrogel Tissue:

For staining of 1 mm-thick brain tissue, the tissue was sectioned using a mouse brain matrix (RBM-2000C; ASI Instruments, Warren, Mich.) after the hydrogel tissue embedding step. 100 μm-thick sections were obtained with a vibratome (VT1200S; Leica, Buffalo Grove, Ill.). The tissue blocks were passively cleared by incubating in 50 mL clearing solution at 37° C. with gentle shaking until fully cleared. Cleared tissue blocks were then placed into a 24 well plate and washed with staining buffer solutions (indicated in each figure) three times, two hours each. Then the tissue blocks were incubated in the same staining buffer solution and washed three times before imaging. For indirect immunostaining, the previous step was repeated for secondary antibodies after primary antibodies. All washing and staining processes were done at room temperature with gentle shaking. Stained sections were then optically cleared and imaged or directly imaged.

eTANGO Solution Preparation:

Prepare non-binding and binding buffers of choice. The following buffers were used (1) pH 11 LB buffer+SDS that contained 50 mM lithium hydroxide, 10 mM SDS, 1% Triton-X 100, and 0.02% sodium azide and was titrated with boric acid to pH 11; (2) pH 11 LB buffer that contained 50 mM lithium hydroxide, 1% Triton-X 100, and 0.02% sodium azide and was titrated with boric acid to pH 11; (3) pH 9 LB buffer that contained 50 mM lithium hydroxide, 1% Triton-X 100, and 0.02% sodium azide and was titrated with boric acid to pH 9; (4) pH 7.5 TB buffer that contained 50 mM Trizma base (Sigma T6066), and 0.02% sodium azide and was titrated with boric acid to pH 7.5.

eTANGO System Construction:

eTANGO device, sample chamber, and associated accessories (chamber cap, motor, and motor controller) were custom-made and assembled. The device was constructed as follows. (1) A heat exchanger was made by immersing 2 meters of ¼" rigid, thin-walled tubing (McMaster-Carr) in a refrigerated bath circulator (WiseCircu WCR-P8, 1.6 kW; Wisd Laboratory Instruments; Germany) set to 1° C.; (2) Nanoporous membranes was mounted to the sample chamber using an electricity-resistant epoxy glue (Hysol ES 1901; Henkel). Pore size (molecular weight cutoff, i.e., MWCO) of the membrane was smaller than the molecular weight of the desired probe. The following membranes from Spectrum Laboratories (Compton, Calif.) were used MWCO of 1 kDa for antibodies, MWCO 6-8 kDa for antibodies and lectins; MWCO 100-500 Da for PO-PRO-1. (3) The system was connected in the following order (in the direction of flow): pump (40PX, PanWorld, Japan), heat exchanger, eTANGO chamber, and reservoir. The heat exchanger was placed directly before eTANGO chamber for efficient cooling. All components were connected with appropriately sized tubing (⅛", ⅜"). (4) The eTANGO device was placed on top of a magnetic stirring plate (HI 190M, Hanna Instruments, RI) and a small stirring bar was added (30620-416; VWR). In some instances, a nylon mesh (CMN-0074-D, Small Parts) was used to build a wall around the tissue holder to secure the tissue in place. The measured temperature of the outer solution was 10-13° C.

eTANGO Process:

The eTANGO process was performed using the following steps. (1) Wash cleared hydrogel tissue in non-binding buffer 2-3 times at room temperature for a day with gentle shaking to equilibrate the tissue with non-binding buffer. Alternatively, tissue can be electrophoretically washed with the eTANGO device to reduce time for washing. (2) Fill the reservoir with non-binding buffer, close the device, and start circulation. Wait until the solution cools down to 10-13° C. (3) Place the tissue inside the chamber and load the chamber with non-binding buffer with 3% bovine serum albumin (BSA). Just enough buffer solution (3-5 ml of buffer solution) was used to immerse the tissue in the solution. (4) Apply electric field for 10 min to disperse BSA in the chamber. (5) Add molecular probes to tissue chamber. (6) Insert the tissue chamber to the eTANGO device and apply 50 V across the chamber for 6 hours. During this step, probe molecules become evenly distributed throughout the porous CLARITY-processed tissue. Running time may vary depending on the parameters described above as well as the size, shape, and density of the sample and concentration, charge state/electromobility of the probe molecules. (6) After the probe-distribution step under non-binding condition, switch the buffer to the binding buffer and continue applying the electric field for another 6 hours or overnight. Buffer composition inside the chamber will equilibrate with the binding buffer outside the chamber. During this step, dispersed probe molecules will bind to targets. This non-binding/binding cycle can be repeated several times to enhance uniformity of staining. (7) For washing, switch the buffer to non-binding buffer again, replace the solution inside the chamber to a fresh non-binding buffer without antibodies, and apply electric field. Replace the solution every hour to enhance wash of unbound antibodies. (8) For indirect immunostaining (or relevant multi-step staining procedure), repeat from step (3) with secondary antibodies.

(9) After immunostaining, incubate the tissue sample in ~50 ml of 10 mM LB, 200 mM SDS (pH 8-9) overnight at room temperature on a shaker.

Optical Clearing with PROTOS:

PROTOS (pH/Refractive index/Osmolarity Tunable Optical-clearing Solution) was made by dissolving 75 g diatrizoic acid (D92681 Sigma-Aldrich), 70 g d-sorbitol (S1876; Sigma-Aldrich), and 23 g n-methyl-d-glucamine (M2004; Sigma-Aldrich) per 100 mL of UltraPure water. Processed samples were incubated in 10 mL PROTOS for 2-3 days at room-temperature with gentle shaking (replacing the solution after each day) for refractive index-matching and imaging. The listed proportions were chosen in order to obtain a near-neutral pH, a refractive index near 1.46, and an osmolarity that reverses tissue-expansion observed during clearing. More basic solutions could be obtained by the addition of larger quantities of n-methyl-d-glucamine and the osmolarity may be lowered by substituting additional d-sorbitol in place of diatrizoic acid. Refractive index was measured using an Abbemat WR/MW automatic multiwavelength refractometer (Anton Paar, Va.).

Tissue Deformation Experiment:

To assess the extent to which stochastic electrotransport deforms tissue samples, a cleared brain tissue was placed in eTANGO device and subjected to 50 V with rotation in pH 11 LB buffer. For 1D electrophoresis only, another tissue was positioned in eTANGO device in such a way that lateral sides (but not dorsal and ventral surfaces) were close to the electrodes and was not rotated.

Gel/BSA-FITC Experiment:

To experimentally test stochastic electrotransport through hydrogel, a disk-shape polyacrylamide gel (radius, 9 mm; height, 8 mm) was made from a solution of 4% acrylamide, 0.07% bis-acrylamide, 0.25% azo-initiator and 1×PBS in UltraPure water (all wt./vol). The solution was degassed and polymerized in 15 ml conical tube as described for CLARITY procedure above, and the resulting cylindrical gel was cut to ~8 mm-thick disks by razor blades. eTANGO sample chamber was loaded with BSA-FITC solution (1 mg/ml in pH 7.5 TB) with rounded side of disk-shape gel touching the bottom of the chamber, and flat sides standing upright. pH 7.5 TB was circulated throughout the setup. 200 V was then applied for 1 hr or 3 hrs to transport BSA-FITC into the gel. 3 mm-thick cross-section from the middle was then obtained using a rat brain matrix and imaged with a fluorescence stereomicroscope.

Mounting and Imaging of CLARITY- or eTANGO-Processed Mouse Brain Tissue:

After incubation in PROTOS, the sample was mounted between a slide glass and a Willco dish (14032-120; Ted Pella). A piece of Blu-Tack adhesive (Blu-tack via Amazon) was rolled into cylinder shapes of a thickness slightly more than that of the sample and was placed in a U-shape on the slide glass. The sample was then carefully placed inside the Blu-Tack and a Willco dish was firmly pressed down onto the adhesive (lipped side facing up) until it just came in contact with the sample. PROTOS was then injected into the void space between adhesive until the imaging chamber was filled without introducing air bubbles. An epoxy glue (Hysol ES 1901; Henkel) was then used to fill the gap in the Blu-Tack to build a wall and seal in the sample. Two microscope systems were used. While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
an electric field generator configured to produce a static electric field;
a chamber capable of being positioned in a field provided by the generator, wherein at least one wall of the chamber comprises a semipermeable material;
a sample positioner in the chamber, wherein the sample positioner is configured to hold a matrix;
an outer chamber capable of retaining a fluid that surrounds at least a portion of the chamber, wherein the outer chamber and the chamber are in fluid communication only via the semipermeable membrane; and
a control system configured to move the sample positioner in the static electric field provided by the electric field generator in a manner that allows the matrix to experience an electrodynamic field.

2. An article as in claim 1, wherein the electric field generator comprises two or more electrodes.

3. An article as in claim 1, wherein the chamber is positioned between two electrodes.

4. An article as in claim 1, wherein the chamber is capable of retaining a fluid.

5. An article as in claim 1, wherein the ratio of a cross-sectional area of the chamber to the cross-sectional area of the sample positioner is greater than or equal to about 20:1.

6. An article as in claim 1, wherein the molecular weight cutoff of the semipermeable material is between about 500 g/mol and about 10,000 g/mol.

7. An article as in claim 1, wherein the semipermeable material is a porous material and wherein the semipermeable material is configured to be substantially impermeable to at least one molecule.

8. An article as in claim 1, wherein the semipermeable material is a porous material having an average pore size of between about 0.001 microns and about 1 micron.

9. An article as in claim 1, comprising a temperature controller connected to the chamber.

10. An article as in claim 1, comprising a fluid inlet and a fluid outlet connected to the chamber.

11. An article as in claim 1, wherein the matrix is a biological matrix.

12. An article of claim 1, wherein the sample positioner is configured to hold a charged matrix.

13. An article of claim 12, wherein the charged matrix comprises a tissue.

14. An article as in claim 1, wherein the field provided by the generator has a magnitude of greater than or equal to 10 V/m.

15. An article as in claim 1, wherein two walls of the chamber comprise the semi-permeable material.

16. An article as in claim 1, comprising a fluid circulator.

17. An article as in claim 1, wherein the matrix comprises a tissue.

18. An article as in claim 1, wherein the matrix comprises a hydrogel.

* * * * *